(12) United States Patent
Ford et al.

(10) Patent No.: US 10,543,211 B2
(45) Date of Patent: Jan. 28, 2020

(54) METHODS AND COMPOSITIONS FOR TREATING DISEASES AND CONDITIONS

(71) Applicant: Afferent Pharmaceuticals, Inc., San Mateo, CA (US)

(72) Inventors: Anthony P. Ford, Palo Alto, CA (US); Julian Paton, Bristol (GB)

(73) Assignee: Afferent Pharmaceuticals, Inc., San Mateo, CA (US)

( * ) Notice: Subject to any disclaimer, the term of this patent is extended or adjusted under 35 U.S.C. 154(b) by 0 days.

(21) Appl. No.: 16/211,409

(22) Filed: Dec. 6, 2018

(65) Prior Publication Data

US 2019/0175593 A1    Jun. 13, 2019

Related U.S. Application Data

(62) Division of application No. 15/323,619, filed as application No. PCT/US2015/039067 on Jul. 2, 2015, now Pat. No. 10,195,198.

(60) Provisional application No. 62/120,643, filed on Feb. 25, 2015, provisional application No. 62/020,839, filed on Jul. 3, 2014.

(51) Int. Cl.
*A61K 31/505* (2006.01)

(52) U.S. Cl.
CPC .................. *A61K 31/505* (2013.01)

(58) Field of Classification Search
CPC .................................. A61K 31/505
USPC ....................................... 514/272
See application file for complete search history.

(56) References Cited

U.S. PATENT DOCUMENTS

| 5,420,129 A | 5/1995 | Breu et al. |
| 2007/0049534 A1 | 3/2007 | Dillon et al. |
| 2007/0049609 A1 | 3/2007 | Broka et al. |
| 2007/0281908 A1 | 12/2007 | Liang et al. |
| 2008/0207619 A1 | 8/2008 | Dillon et al. |
| 2011/0269961 A1 | 11/2011 | Dvorak et al. |

FOREIGN PATENT DOCUMENTS

WO    2011062550 A1    5/2011

OTHER PUBLICATIONS

"AF-353, a novel, potent and orally bioavailable P2X3/P2X2/3 receptor antagonist.", British Journal of Pharmacology Jul. 2010, vol. 160, No. 6, Jul. 2010 (Jan. 2010), pp. 1387-1398, ISSN: 1476-5381.
"In pursuit of P2X3 antagonists: novel therapeutics for chronic pain and afferent sensitization", Purinergic Signalling, Kluwer Academic Publishers, DO, vol. 8, No. Suppl 11, Feb. 2012, pp. S3-S26, XP002699076, ISSN: 1573-9546, DOI: 10.1007/S11302-011-9271-6.
"Ventilatory and carotid body chemoreceptor responses to purinergic P2X receptor antagonists in newborn rats", Journal of Applied Physiology, vol. 110, No. 1, Jan. 2011 (Jan. 2011), pp. 83-94, ISSN: 8750-7587.
Beers, et al., The Merck Index of Medical Information 2nd Edition, p. 31 (2003).
Egan, et al., Prevalence of Optimal Treatment Regimens in Patients with Apparent Treatment-Resistant Hypretension Based on Office Blood Pressure in a Community-Based Practice Network, NPL-EGAN-2013-691, 2013, pp. 691-697, 62, No. 4.
U.S. Appl. No. 15/323,619, filed Jan. 3, 2017.

*Primary Examiner* — Kevin E Weddington
(74) *Attorney, Agent, or Firm* — Yong Zhao; Anna L. Cocuzzo; Catherine D. Fitch

(57) ABSTRACT

Provided herein include methods and compositions for treating diseases or conditions. In some embodiments provided are methods for treating one or more diseases or conditions selected from the group consisting of hypertension, heart failure, dyspnea, and sleep apnea. In certain embodiments provided are methods that include administering a compound of formula (I) as disclosed herein. In some embodiments provided are methods that include administering a P2X3 and/or a P2X2/3 receptor antagonist.

20 Claims, 7 Drawing Sheets

METHODS AND COMPOSITIONS FOR TREATING DISEASES AND CONDITIONS

CROSS REFERENCE

This application is a Division of Application No. 15/323,619, filed Jan. 3, 2017, which is a U.S. National Phase application under 35 U.S.C. § 371 of PCT Application No. PCT/US2015/039067, filed Jul. 2, 2015, which published as WO 2016/004358 A1 on Jan. 7, 2016, and claims priority to and the benefit of U.S. Provisional Patent Application Ser. No. 62/020,839, filed on Jul. 3, 2014, and U.S. Provisional Patent Application Ser. No. 62/120,643, filed on Feb. 25, 2015, each of which is incorporated by reference herein in its entirety.

FIELD OF THE INVENTION

The present disclosure relates to the field of altering physiological conditions and or treating diseases.

BACKGROUND

The information provided herein and references cited are provided solely to assist the understanding of the reader, and does not constitute an admission that any of the references or information is prior art to the present invention.

U.S. patent application Ser. No. 11/906,802 (Patented as U.S. Pat. No. 8,003,788) discloses methods and intermediates for the preparation of compounds that are P2X3 and P2X2/3 receptor modulators. U.S. application Ser. No. 11/187,753 discloses methods of diagnosing and treating pulmonary diseases using certain specific P2 receptor modulators.

SUMMARY

The present disclosure relates to the field of altering physiological conditions and/or treating diseases.

In a first aspect, provided is a method of treating hypertension in a subject involving identifying a subject diagnosed with hypertension and administering to the subject a compound formula (I), such as, for example, one or more compounds selected from the group consisting of the compounds of Table 1.

The term "hypertension" as used herein refers to a condition or disease well known in the art in which the blood pressure in a mammal is chronically elevated. In certain embodiments hypertension may refer to a condition in which a subject's resting systolic blood pressure is above about 120 mmHg and/or diastolic pressure is above about 80 mmHg. In certain embodiments hypertension may refer to a condition in which a subject's resting systolic blood pressure is above about 115 mmHg; or above about 120 mmHg; or above about 125 mmHg; or above about 130 mmHg; or above about 135 mmHg; or above about 140 mmHg; or above about 145 mmHg; or above about 150 mmHg; or above about 155; or above about 160; or above about 165; or above about 170 and/or resting diastolic pressure is above about 75 mmHg; or above about 80 mmHg; or above about 85 mmHg; or above about 90 mmHg; or above about 95 mmHg; or above about 100 mmHg; or above about 105 mmHg; or above about 110 mmHg. In some embodiments hypertension may be primary or secondary hypertension. In some embodiments hypertension may be chronic treatment resistant hypertension, defined as persistent hypertension (resting office blood pressure >140/90 [SBP/DBP]) despite use of >3 antihypertensive medications including a diuretic, as well as hypertension in patients unable to tolerate currently preferred antihypertensive medications, or in whom approved medications cannot achieve recommended levels of BP control. Diagnosis of hypertension in a subject may in various embodiments be performed by an individual qualified to make such diagnosis in a particular jurisdiction.

In another aspect, provided is a method of treating heart failure in a subject involving identifying a subject diagnosed with heart failure and administering to the subject a compound formula (I), such as, for example, one or more compounds selected from the group consisting of the compounds of Table 1.

The term "heart failure" as used herein refers to a condition or disease well known in the art which is associated with the heart being unable to maintain blood flow sufficient to maintain the needs of the body. Diagnosis of heart failure may in certain embodiments be based on echocardiography results characteristic of heart failure. In some embodiments, heart failure may refer to a condition often referred to as congestive heart failure. In some embodiments, heart failure may refer to systolic heart failure, also called heart failure due to reduced ejection fraction (HFREF) or heart failure due to left ventricular systolic dysfunction. In some embodiments, heart failure may refer to heart failure with preserved ejection fraction (HFPEF) also known as diastolic heart failure or heart failure with normal ejection fraction (HFNEF). In some embodiments, heart failure may be chronic heart failure and in other embodiments the heart failure may be acute heart failure. Diagnosis of heart failure in a subject may in various embodiments be performed by an individual qualified to make such diagnosis in a particular jurisdiction.

In a further aspect, provided is a method of treating dyspnea in a subject involving identifying a subject diagnosed with dyspnea and administering to the subject a compound formula (I), such as, for example, one or more compounds selected from the group consisting of the compounds of Table 1.

The term "dyspnea" as used herein refers to a condition or disease well known in the art in which a subject experiences feelings or sensations associated with impaired breathing. In some embodiments dyspnea may refer to a condition consistent with the America Thoracic Society definition of dyspnea, i.e., "a subjective experience of breathing discomfort that consists of qualitatively distinct sensations that vary in intensity". In some embodiments dyspnea may refer to sensations of inadequate breathing, uncomfortable awareness of breathing and/or breathlessness. Diagnosis of dyspnea in a subject may in various embodiments be performed by an individual qualified to make such diagnosis in a particular jurisdiction.

In another aspect, provided is a method of treating sleep apnea in a subject involving identifying a subject diagnosed with sleep apnea and administering to the subject a compound formula (I), such as, for example, one or more compounds selected from the group consisting of the compounds of Table 1.

The term "sleep apnea" as used herein refers to a condition or disease well known in the art characterized by disruptions in breathing (e.g., pauses in breathing or instances of shallow or infrequent breathing) during sleep. In some aspects sleep apnea is central sleep apnea, obstructive sleep apnea, or mixed sleep apnea. In some embodiments, sleep apnea may be characterized by more than about 5 apneic events per hour of sleep; or more than about 10 apneic events per hour of sleep; or more than about 15 apneic events per hour sleep; or more than about 20 apneic events per hour of sleep, or more than about 25 apneic events per hour of sleep, or more than about 30 apneic sleep events per hour sleep; or more than about 35 apneic sleep events per hour sleep. Diagnosis of dyspnea in a subject may in various embodiments be performed by an individual qualified to make such diagnosis in a particular jurisdiction.

In one aspect, provided is a method for altering carotid body tonicity or activity in a subject, involving identifying a subject in need of altering carotid body tonicity or activity and administering to the subject a compound formula (I), such as, for example, one or more compounds selected from the group consisting of the compounds of Table 1.

The term "carotid body" as used herein refers to a small cluster of chemoreceptors and supporting cells located near the fork (bifurcation) of the carotid artery. The carotid body is also referred in the art as carotid glomus or glomus caroticum. The term "altering carotid body tonicity" or activity as used herein means modifying the level of excitation of carotid sinus nerve chemoreceptor afferents that are discharging excessively in response to dysregulated levels of arterial chemicals (hyperreflexia), as well as attenuating the aberrant, spontaneous discharge of such nerve fibers that can occur in the absence of chemical dysregulation.

In one aspect, provided is a method for reducing carotid body tonicity in a subject involving identifying a subject in need of reduction in carotid body tonicity or activity and administering to the subject a compound of formula (I), such as, for example, one or more compounds selected from the group consisting of the compounds of Table 1.

In an additional aspect, provided is a method of reducing carotid body chemosensory afferent discharge in a subject involving identifying a subject in need of reduction in carotid body chemosensory afferent discharge and administering to the subject a compound formula (I), such as, for example, one or more compounds selected from the group consisting of the compounds of Table 1.

The term "carotid body chemosensory afferent discharge" as used herein means the electrical generation of action potentials from peripheral carotid sinus nerve terminals abutting glomus cells in the carotid body, and their orthograde propagation to petrosal ganglion perikarya as well as afferent central terminal projections located within the medullary nucleus tractus solitarius (NTS) in the brainstem.

The term "a compound of formula (I) as used herein refers to compounds having a structure of the below formula (I):

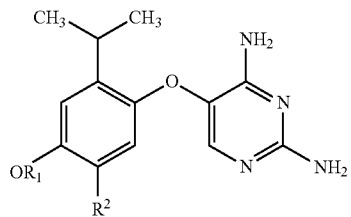

or a pharmaceutically acceptable salt thereof.

In some embodiments, $R^1$ is hydrogen or optionally substituted alkyl, and $R^2$ is alkyl; alkenyl; alkynyl; amino; aminosulfonyl; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; carboxyalkyl; cyano or alkylcarbonyl. In one or more embodiments of any aspects of the invention, $R^1$ can be methyl or $R^1$ can be hydrogen. In one or more embodiments $R^2$ can be haloalkyl, aminosulfonyl, alkylsulfonyl, alkylcarbonyl or carboxyalkyl. In some embodiments, $R^2$ is haloalkyl, wherein the alkyl is methyl.

In some embodiments, $R^2$ is aminosulfonyl. $R^2$ is carboxyalkyl or $R^2$ is alkylcarbonyl. In certain embodiments of formula (I), $R^1$ is methyl. In certain embodiments of formula (I), $R^1$ is hydrogen. In certain embodiments of formula (I), $R^2$ is haloalkyl, aminosulfonyl, alkylsulfonyl, alkylcarbonyl or carboxyalkyl. In certain embodiments of formula (I), $R^2$ is haloalkyl, where alkyl is methyl. In certain embodiments of formula (I), $R^2$ is aminosulfonyl. In certain embodiments of formula (I), $R^2$ is carboxyalkyl. In certain embodiments of formula (I), $R^2$ is alkylcarbonyl. Where $R^1$, or $R^2$, is alkyl or contains an alkyl moiety, such alkyl is preferably lower alkyl, i.e. $C_1$-$C_6$alkyl, and more preferably $C_1$-$C_4$alkyl. Compounds of formula I may be synthesized for example as disclosed in U.S. Pat. No. 8,808,313. In some embodiments, a compound of formula (I) is a compound selected from Table 1.

The term "subject" as used herein refers to a biological organism. In certain embodiments a subject may be a mammal or non-mammal animal. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex. In certain embodiments the individual may be a patient, i.e., an subject that is a candidate for, or awaiting, medical or other treatment, such as, e.g., the methods as described herein. A patient may, in some embodiments, be a human patient or a veterinary patient.

The terms "treating," "treat," "treatment," "treatable" and the like refer to: modulating (e.g., preventing or reducing) a disease, disorder or condition from occurring in a cell, a tissue, a system, animal or subject; stabilizing a disease, disorder or condition, i.e., arresting its development; and/or modulating (e.g., reducing or alleviating) one or more symptoms of the disease, disorder or condition, i.e., causing regression of the disease, disorder and/or condition. It is understood that the term "treating" as contemplated herein is used in the context of a statistical sample or an average subject and in some embodiments may not require an observable effect in all subjects or samples subjected to a particular therapeutic, agent (such as a P2X3 or P2X2/3 modulator) or method. The term treating or treatment as used herein may in certain embodiments involve a step of identifying a subject as having, being suspected of having and/or being diagnosed with a disease or condition to be treated. As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. It is understood that the term "prevents" as contemplated herein is used in the context of a statistical sample or an average subject and in some embodiments may not require an observable effect in all subjects or samples subjected to a particular therapeutic or agent.

"Therapeutically effective amount" or "effective amount" means an amount of a compound or agent (such as, e.g., a P2X3 and/or P2X2/3 modulator) that, when administered to a subject for a particular purpose, is sufficient to modulate such intended purpose. The "therapeutically effective amount" will vary depending on the compound, disease state being treated, the severity or the disease treated, the age and relative health of the subject, the route and form of administration, the judgment of the attending medical or veterinary practitioner, and other factors. It is understood that the term "therapeutically effective amount" as contemplated herein is used in the context of a statistical sample or an average subject and in some embodiments may not require an observable effect in all subjects or samples subjected to a particular compound or agent. In various aspects and embodiments contemplated herein, administering a compound refers to administering a therapeutically effective amount of such compound.

The term "about" as used herein means in quantitative terms plus or minus 10%. For example, "about 3%" would encompass 2.7-3.3% and "about 10%" would encompass 9-11%. In some embodiments the term about means in quantitative terms plus or minus 8%; or 5% or 3% or 1%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

BRIEF DESCRIPTION OF THE DRAWINGS

FIG. 1A shows the effects of Compound A, on carotid sinus nerve activity and excitatory responses to hypoxia and ATP (or analogs), in a wild-type mouse. FIG. 1B shows the effects of Compound A on carotid sinus nerve activity and excitatory responses to hypoxia and ATP (or analogs) in a P2X2-gene deletion mutant (P2X2KO) mouse.

DETAILED DESCRIPTION

Figure 1A:
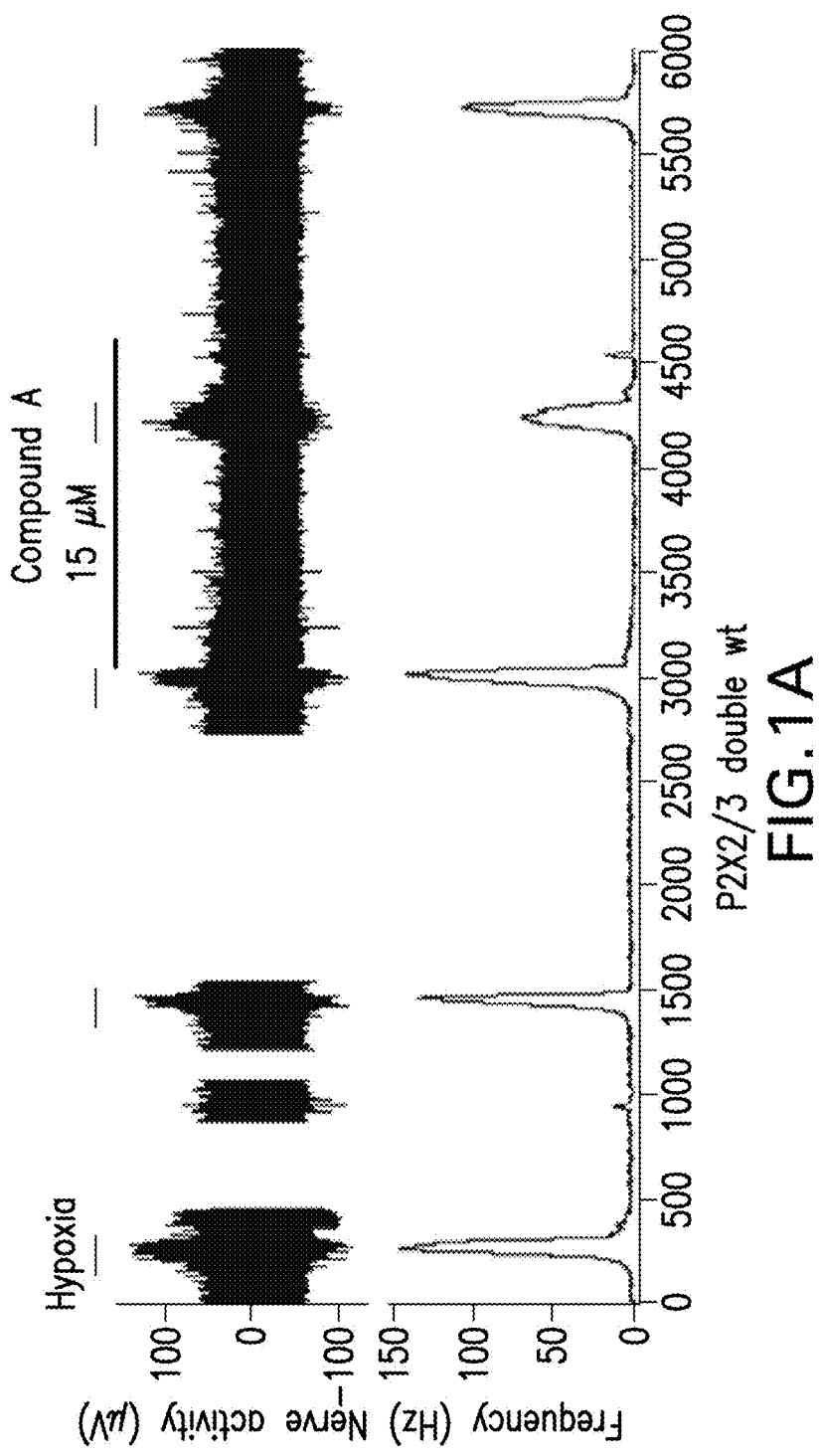
FIGS. 1A and 1B shows a proof-of-concept experiment involving compound A.

Certain aspects, embodiments and/or methods described herein are based at least in part on the surprising finding that compounds of formula (I) have surprising affects on certain diseases and conditions.

Non-limiting exemplary compounds in accordance with the methods, technologies and disclosures provided herein are shown in Table 1.

TABLE 1

| # | Structure | Name |
|---|---|---|
| 1 | 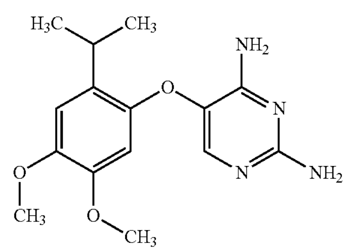 [SMILES: COc1cc(Oc2cnc(N)nc2N)c(C(C)C)cc1OC] | 5-(2-Isopropyl-4,5-dimethoxy-phenoxy)-pyrimidine-2,4-diamine |
| 2 | 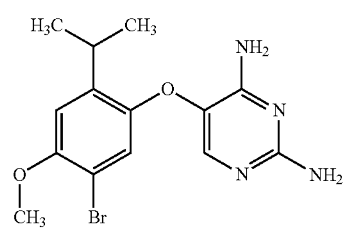 | 5-(5-Bromo-2-isopropyl-4-methoxy-phenoxy)-pyrimidine-2,4-diamine |
| 3 | 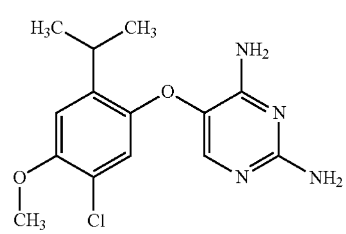 | 5-(5-Chloro-2-isopropyl-4-methoxy-phenoxy)-pyrimidine-2,4-diamine |

TABLE 1-continued

| # | Structure | Name |
|---|---|---|
| 4 | 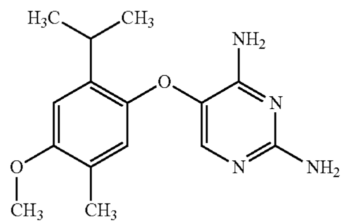 | 5-(2-Isopropyl-4-methoxy-5-methyl-phenoxy)-pyrimidine-2,4-diamine |
| 5 | 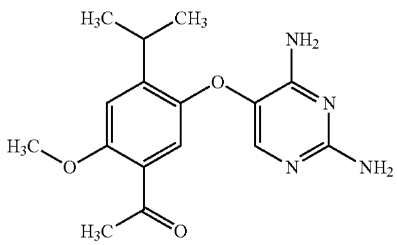 [SMILES: COc1cc(C(C)C)c(Oc2cnc(N)nc2N)cc1C(C)=O] | 1-[5-(2,4-Diamino-pyrimidin-5-yloxy)-4-isopropyl-2-methoxy-phenyl]-ethanone |
| 6 | 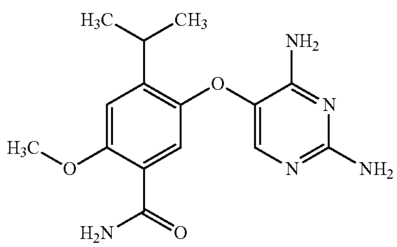 [SMILES: COc1cc(C(C)C)c(Oc2cnc(N)nc2N)cc1C(N)=O] | 5-(2,4-Diamino-pyrimidin-5-yloxy)-4-isopropyl-2-methoxy-benzamide |
| 7 | 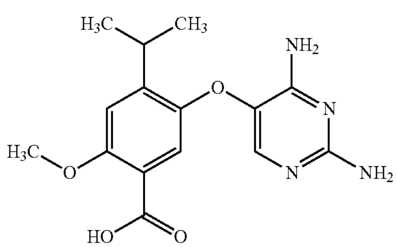 [SMILES: COc1cc(C(C)C)c(Oc2cnc(N)nc2N)cc1C(=O)O] | 5-(2,4-Diamino-pyrimidin-5-yloxy)-4-isopropyl-2-methoxy-benzoic acid |
| 8 | 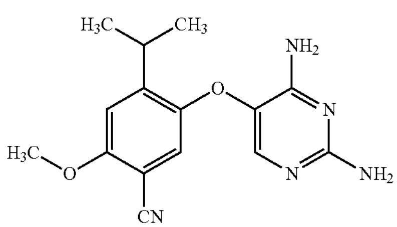 [SMILES: COc1cc(C(C)C)c(Oc2cnc(N)nc2N)cc1C#N] | 5-(2,4-Diamino-pyrimidin-5-yloxy)-4-isopropyl-2-methoxy-benzonitrile |
| 9 | 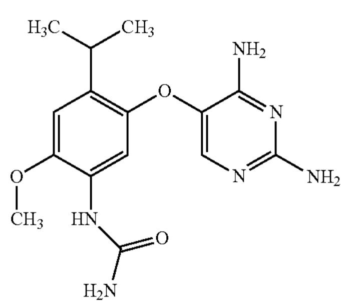 [SMILES: COc1cc(C(C)C)c(Oc2cnc(N)nc2N)cc1NC(N)=O] | [5-(2,4-Diamino-pyrimidin-5-yloxy)-4-isopropyl-2-methoxy-phenyl]-urea |

TABLE 1-continued

| # | Structure | Name |
|---|-----------|------|
| 10 | 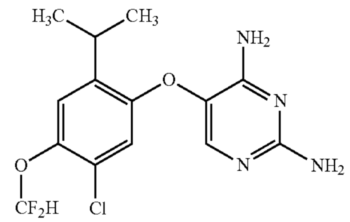 [SMILES: CC(C)c1cc(OC(F)F)c(Cl)cc1Oc1cnc(N)nc1N] | 5-(5-Chloro-4-difluoromethoxy-2-isopropyl-phenoxy)-pyrimidine-2,4-diamine |
| 11 | 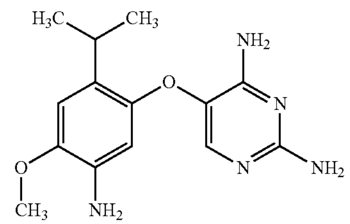 | 5-(5-Amino-2-isopropyl-4-methoxy-phenoxy)-pyrimidine-2,4-diamine |
| 12 | 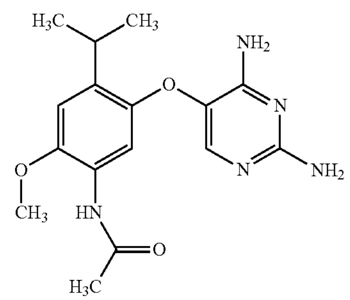 [SMILES: COc1cc(C(C)C)c(Oc2cnc(N)nc2N)cc1NC(C)=O] | N-[5-(2,4-Diamino-pyrimidin-5-yloxy)-4-isopropyl-2-methoxy-phenyl]-acetamide |
| 13 | 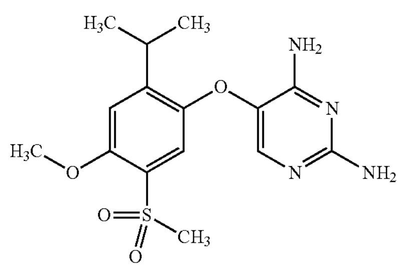 [SMILES: COc1cc(C(C)C)c(Oc2cnc(N)nc2N)cc1S(C)(=O)=O] | 5-(2-Isopropyl-5-methanesulfonyl-4-methoxy-phenoxy)-pyrimidine-2,4-diamine |
| 14 | 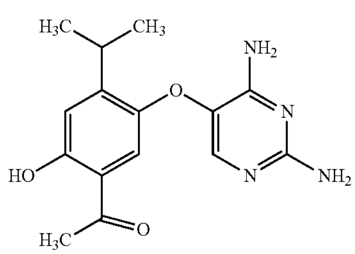 [SMILES: CC(=O)c1cc(Oc2cnc(N)nc2N)c(C(C)C)cc1O] | 1-[5-(2,4-Diamino-pyrimidin-5-yloxy)-2-hydroxy-4-isopropyl-phenyl]-ethanone |
| 15 | 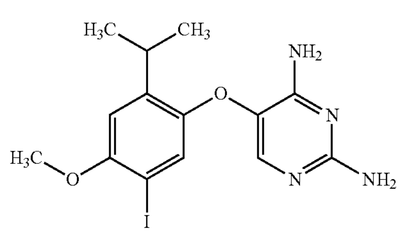 | 5-(5-Iodo-2-isopropyl-4-methoxy-phenoxy)-pyrimidine-2,4-diamine |

TABLE 1-continued

| # | Structure | Name |
|---|---|---|
| 16 | 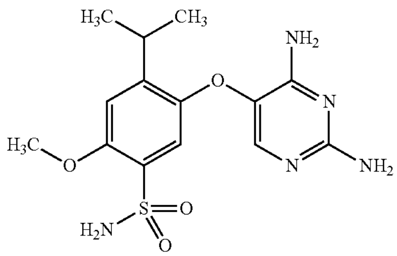 [SMILES: COc1cc(C(C)C)c(Oc2cnc(N)nc2N)cc1S(N)(=O)=O] | 5-(2,4-Diamino-pyrimidin-5-yloxy)-4-isopropyl-2-methoxy-benzenesulfonamide |
| 17 | 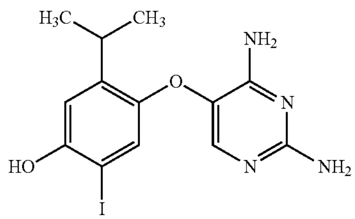 [SMILES: CC(C)c1cc(O)c(I)cc1Oc1cnc(N)nc1N] | 4-(2,4-Diamino-pyrimidin-5-yloxy)-2-iodo-5-isopropyl-phenol |
| 18 | 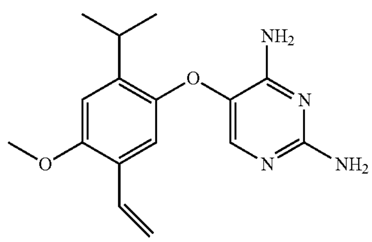 [SMILES: C=Cc1cc(Oc2cnc(N)nc2N)c(C(C)C)cc1OC] | 5-(2-Isopropyl-4methoxy-5-vinyl-phenoxy)-pyrimidine-2,4-diamine |
| 19 | 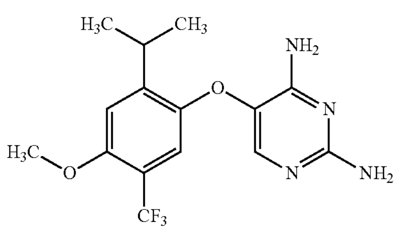 | 5-(2-Isopropyl-4-methoxy-5-trifluoromethyl-phenoxy)-pyrimidine-2,4-diamine |
| 20 | 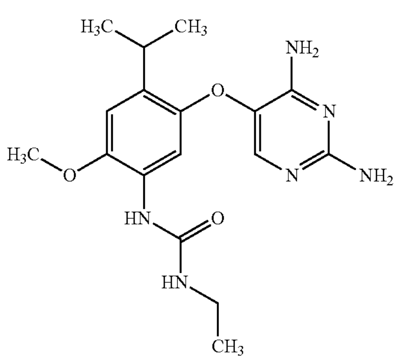 [SMILES: CCNC(=O)Nc1cc(Oc2cnc(N)nc2N)c(C(C)C)cc1OC] | 1-[5-(2,4-Diamino-pyrimidin-5-yloxy)-4-isopropyl-2-methoxy-phenyl]-3-ethyl-urea |
| 21 | 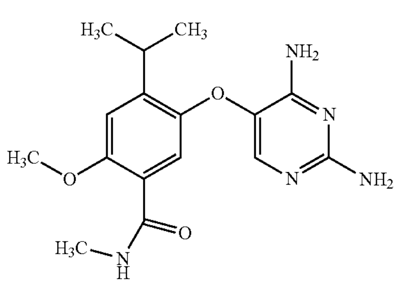 [SMILES: CNC(=O)c1cc(Oc2cnc(N)nc2N)c(C(C)C)cc1OC] | 5-(2,4-Diamino-pyrimidin-5-yloxy)-4-isopropyl-2-methoxy-N-methyl-benzamide |

TABLE 1-continued
| # | Structure | Name |
|---|---|---|
| 22 | 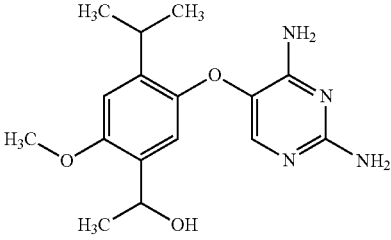 | 1-[5-(2,4-Diamino-pyrimidin-5-yloxy)-4-isopropyl-2-methoxy-phenyl]-ethanol |
| 23 | 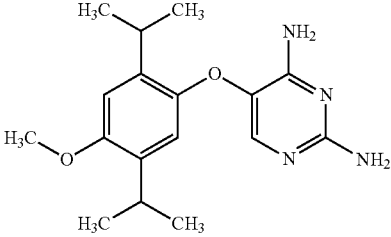 [SMILES: COc1cc(C(C)C)c(Oc2cnc(N)nc2N)cc1C(C)C] | 5-(2,5-Diisopropyl-4-methoxy-phenoxy)-pyrimidine-2,4-diamine |
| 24 | 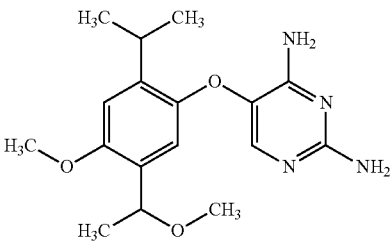 [SMILES: COc1cc(C(C)C)c(Oc2cnc(N)nc2N)cc1C(C)OC] | 5-[2-Isopropyl-4-methoxy-5-(1-methoxy-ethyl)-phenoxy]-pyrimidine-2,4-diamine |
| 25 | 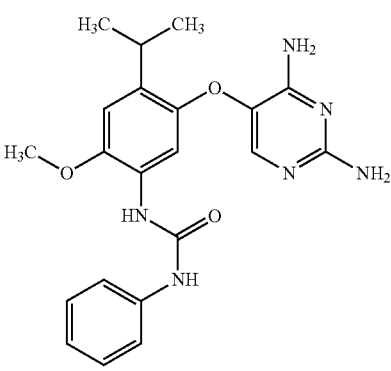 [SMILES: COc1cc(C(C)C)c(Oc2cnc(N)nc2N)cc1NC(=O)Nc1ccccc1] | 1-[5-(2,4-Diamino-pyrimidin-5-yloxy)-4-isopropyl-2-methoxy-phenyl]-3-phenyl-urea |
| 26 | 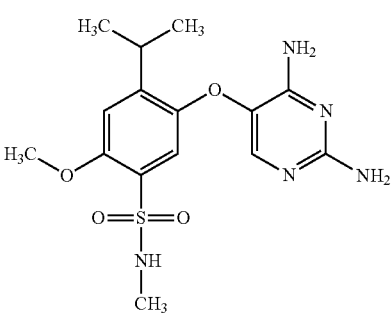 [SMILES: CNS(=O)(=O)c1cc(Oc2cnc(N)nc2N)c(C(C)C)cc1OC] | 5-(2,4-Diamino-pyrimidin-5-yloxy)-4-isopropyl-2-methoxy-N-methyl-benzenesulfonamide |

TABLE 1-continued

| # | Structure | Name |
|---|---|---|
| 27 | 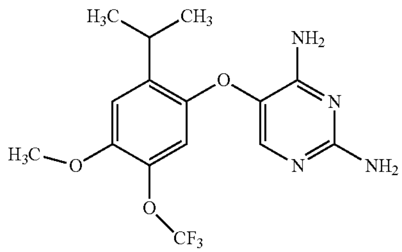 [SMILES: COc1cc(C(C)C)c(Oc2cnc(N)nc2N)cc1OC(F)(F)F] | 5-(2-Isopropyl-4-methoxy-5-trifluoromethoxy-phenoxy)-pyrimidine-2,4-diamine |
| 28 | 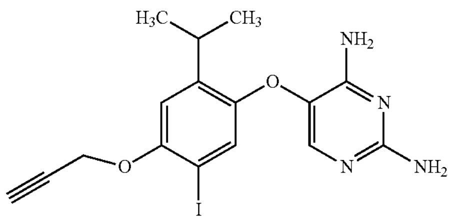 [SMILES: C#CCOc1cc(C(C)C)c(Oc2cnc(N)nc2N)cc1I] | 5-(5-Iodo-2-isopropyl-4-prop-2-ynyloxy-phenoxy)-pyrimidine-2,4-diamine |
| 29 | 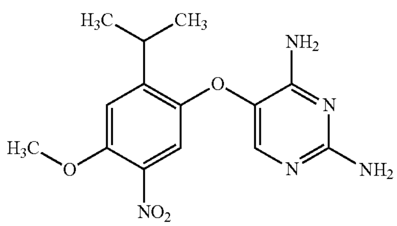 [SMILES: COc1cc(C(C)C)c(Oc2cnc(N)nc2N)cc1[N+](=O)[O-]] | 5-(2-Isopropyl-4-methoxy-5-nitro-phenoxy)-pyrimidine-2,4-diamine |
| 30 | 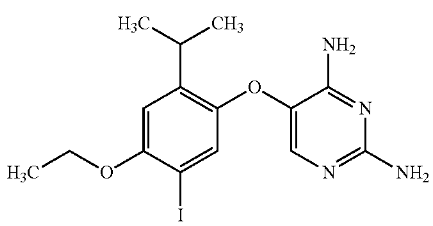 [SMILES: CCOc1cc(C(C)C)c(Oc2cnc(N)nc2N)cc1I] | 5-(4-Ethoxy-5-iodo-2-isopropyl-phenoxy)-pyrimidine-2,4-diamine |
| 31 | 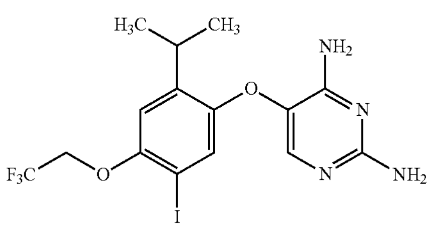 [SMILES: CC(C)c1cc(OCC(F)(F)F)c(I)cc1Oc1cnc(N)nc1N] | 5-[5-Iodo-2-isopropyl-4-(2,2,2-trifluoro-ethoxy)-phenoxy]-pyrimidine-2,4-diamine |
| 32 | 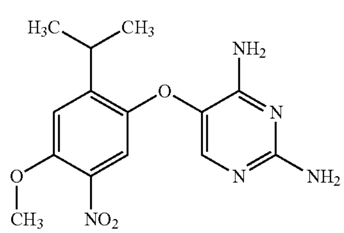 [SMILES: COc1cc(C(C)C)c(Oc2cnc(N)nc2N)cc1[N+](=O)[O-]] | 5-(2-Isopropyl-4-methoxy-5-nitro-phenoxy)-pyrimidine-2,4-diamine |

TABLE 1-continued

| # | Structure | Name |
|---|---|---|
| 33 | 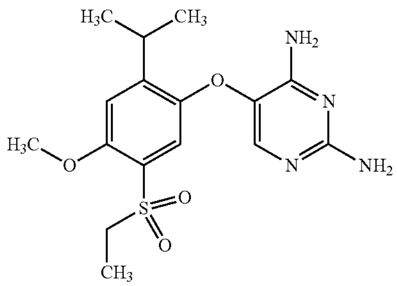 [SMILES: CCS(=O)(=O)c1cc(Oc2cnc(N)nc2N)c(C(C)C)cc1OC] | 5-(5-Ethanesulfonyl-2-isopropyl-4-methoxy-phenoxy)-pyrimidine-2,4-diamine |
| 34 | 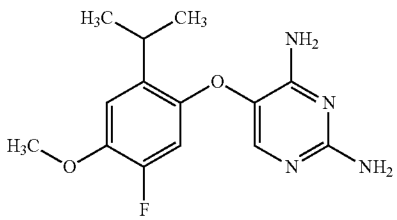 | 5-(5-Fluoro-2-isopropyl-4-methoxy-phenoxy)-pyrimidine-2,4-diamine |
| 35 | 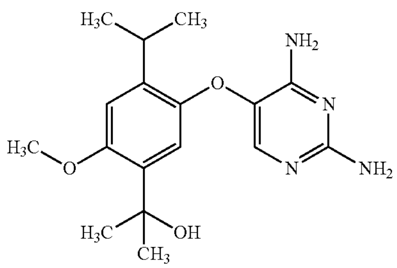 [SMILES: COc1cc(C(C)C)c(Oc2cnc(N)nc2N)cc1C(C)(C)O] | 2-[5-(2,4-Diamino-pyrimidin-5-yloxy)-4-isopropyl-2-methoxy-phenyl]-propan-2-ol |
| 36 | 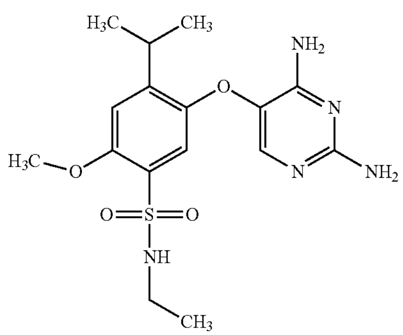 [SMILES: CCNS(=O)(=O)c1cc(Oc2cnc(N)nc2N)c(C(C)C)cc1OC] | 5-(2,4-Diamino-pyrimidin-5-yloxy)-N-ethyl-4-isopropyl-2-methoxy-benzenesulfonamide |
| 37 | 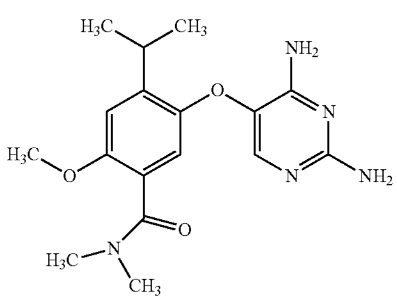 [SMILES: COc1cc(C(C)C)c(Oc2cnc(N)nc2N)cc1C(=O)N(C)C] | 5-(2,4-Diamino-pyrimidin-5-yloxy)-4-isopropyl-2-methoxy-N,N-dimethyl-benzamide |

As used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, e.g., $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is (C=O) and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula —R'—R"—R'" where R' is alkylene, R" is —$SO_2$— and R'" is alkyl as defined herein.

"Alkylamino" means a moiety of the formula —NR—R' wherein R is hydrogen or alkyl and R' is alkyl as defined herein.

"Alkylsulfanyl" means a moiety of the formula —SR wherein R is alkyl as defined herein.

"Amino" means a moiety of the formula —NHR wherein R can be hydrogen or alkyl.

"Amido" means a moiety of the formula —NR(CO)R'— wherein R and R' can be H or alkyl as defined herein.

"Hydroxy" means a moiety of the formula —OH.

"Haloalkoxy" means a group of the formula —OR, wherein R is a haloalkyl group as defined herein.

"Nitro" means a group of the formula —$NO_2$. "Alkylcarbonyl" refers to a group of the formula —(CO)R wherein R is an alkyl group as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminosulfonyl" means a group —$SO_2$—NRR' wherein R and R' each independently is hydrogen or alkyl as defined herein.

"Alkylsulfonylamido" means a moiety of the formula —NR'$SO_2$—R wherein R is alkyl and R' is hydrogen or alkyl.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylsulfonyl" means a group of the formula —$SO_2$—R wherein R is aryl as defined herein.

"Antagonist" refers to a compound that diminishes or prevents the action of another compound or receptor site.

"Cyanoalkyl" means a moiety of the formula —R'—R", where R' is alkylene as defined herein and R" is cyano or nitrile.

The terms "halo", "halogen" and "halide", which may be used interchangeably, refer to a substituent fluoro, chloro, bromo, or iodo.

"Haloalkyl" means alkyl as defined herein in which one or more hydrogen atoms have been replaced with the same or different halogen. Exemplary haloalkyls include —$CH_2Cl$, —$CH_2CF_3$, —$CH_2CCl_3$, perfluoroalkyl (e.g., —$CF_3$), and the like.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Carboxy" means a group of the formula —O—C(O)—OH.

"Sulfonamido" means a group of the formula —$SO_2$—NR'R" wherein R', and R" each independently is hydrogen or alkyl.

"Optionally substituted", for example when used with the term alkyl, means an alkyl group which is optionally substituted independently with one to three substituents, preferably one or two substituents selected from any of the substituents defined herein, for instance: alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that any of the functional groups (e.g., substituents) defined herein can be connected in any orientation relative to the rest of the chemical structure. For instance, an amido group can be connected in either orientation: —R—(CO)NH—R' or —R'(CO)NH—R.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to choose a group for the ease of removal and for the ability to withstand the following reactions.

"Solvates" means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Sympathetic hyperactivity disorder" or "sympathetic disease" refers to, without limitation, hypertension, heart failure, stroke, and the like. "Carotid body hypertonicity disorders" include conditions where tonic discharge of chemosensitive carotid sinus petrosal afferents has developed and drives an unfavorably imbalanced excessive excitatory output of sympathetic tone to cardiovascular structures, for example, in hypertension, heart failure, chronic sleep apnea; and diseases in which common symptoms are persistent and excessive breathlessness (dyspnea) and fatigue, which may include heart failure and chronic obstructive pulmonary disease (COPD).

The terms "those defined above" and "those defined herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

"Primary hypertension," also known as "essential hypertension" or "idiopathic hypertension" is the form of hypertension that by definition, has no identifiable cause.

"Secondary hypertension" or "inessential hypertension" is a type of hypertension which by definition is caused by an identifiable underlying secondary cause. For instance, secondary hypertension can be caused by endocrine diseases, kidney diseases, and tumors. It also can be a side effect of many medications.

Nomenclature and Structures

In general, the nomenclature used in this Application is based on AUTONOM™ v. 4.0; a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

All patents and publications identified herein are incorporated herein by reference in their entirety.

In some embodiments, proof-of-concept experiments are carried out using a test compound, e.g., Compound A:

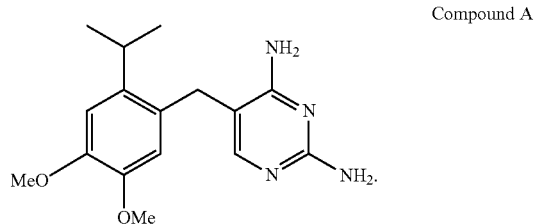 [SMILES: COc1cc(Cc2cnc(N)nc2N)c(C(C)C)cc1OC]

Compound A

Compound A is a benzyl-diaminopyrimidine P2X3 antagonist.

Methods

Certain aspects, embodiments and/or methods described herein are based at least in part on the surprising finding that compounds of formula (I) have surprising affects on certain diseases and conditions such as, for example, hypertension, heart failure, dyspnea, sleep apnea and the like. Accordingly provided herein include methods for treating such diseases using compounds of formula (1), including compounds of Table 1.

The methods provided herein include methods for treating a disease mediated by a P2X3 or P2X2/3 receptor antagonist, said method comprising administering to a subject in need thereof an effective amount of a compound of formula (I):

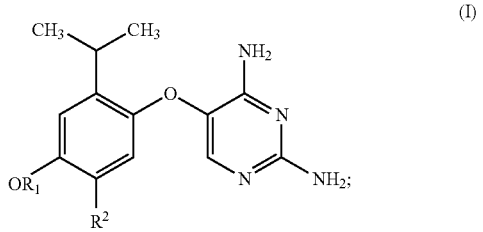

(I)

or a pharmaceutically acceptable salt, solvate, hydrate, or stereoisomer thereof, wherein:

$R^1$ is hydrogen or optionally substituted $C_1$-$C_6$ alkyl;

$R^2$ is: alkyl; alkenyl; alkynyl; amino; aminosulfonyl; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; carboxyalkyl; cyano or alkylcarbonyl.

Peripheral arterial chemosensation plays a critical role in the detection of circulating levels of oxygen, carbon dioxide, pH and other metabolites, allowing maintained homeostatic control of autonomic functions, ventilatory drive and cardiorespiratory control, and protecting against acute deviations in these chemical stimuli. The primary chemosensory cells within the arterial system are glomus (type 1) cells of the carotid bodies, residing at the two carotid bifurcations. Glomus cell activation by reduced arterial $O_2$ or pH and/or elevated $CO_2$ increases communication to adjacent chemosensory afferents within the carotid sinus nerve via release of specific transmitter substances (Fitzgerald et al., 2009, Adv. Exp. Med. Biol., 648: 19-28; Nurse, 2010, Exp. Physiol. 95(6):657-667).

Without wishing to be bound by theory, it is proposed that the sensitivity of this chemosensory mechanism becomes markedly heightened in a variety of pathological conditions, leading to accentuated sensing of chemical changes as well as inappropriate spontaneous tonic discharge (hypertonicity); this sensitization leads to centrally mediated shifts in the balance of autonomic outflow towards increased sympathetic transmission, and triggers common signs and symptoms of many cardiopulmonary and metabolic diseases including chronically increased vascular resistance, cardiac output and blood pressure (Paton et al., 2013, Curr. Hypertens. Rep., 15:273-280), the perception of dyspnea and fatigue, and pro-inflammatory immune activation.

The identity of transmitter substances responsible for sensitizing carotid sinus nerve excitability and contributing to tonic discharge has been the subject of considerable work, with acetylcholine, dopamine, serotonin and ATP, among others, all suspected as participating (Nurse, 2010, Exp. Physiol. 95(6):657-667: Kumar, 2007, Essays Biochem. 43:43-60). In the case of ATP, it is released from chemosensitive glomus cells of the carotid body and is able to excite petrosal sensory nerve endings of the carotid sinus nerve (Zhang et al., 2000, J Physiol., 525: 143-158; Prasad et al., 2001, J Physiol., 537: 667-677; Burnstock, 2009, Handb. Exp. Pharmacol. 194:333-92); recent evidence adds futher support by confirming the release of ATP in human carotid body tissues (Kåhlin J et al., 2014 Exp Physiol (May 30) PMID: 24887113).

Without wishing to be bound by theory, it is proposed that the extracellular signaling functions of ATP result from activation of P2 purinoceptors, which mediate many physiological and pathological roles on all types of cells (See, Burnstock (1993) Drug Dev. Res. 28:195-206). Among these signals, ATP is able to stimulate sensory nerve endings, in particular on small and medium size sensory neurons, resulting in a pronounced increase in sensory nerve discharge and the perception of a variety of unpleasant sensations such as pain, discomfort, fatigue, urinary urgency, itch, urge to cough and breathlessness, mediated largely via activation of receptors containing P2X3 subunits, on afferent nerve fibers innervating many rodent and human tissues (Burnstock, 2009, Handb. Exp. Pharmacol. 194:333-92; Ford and Undem, 2013, Front Cell Neurosci. 7:267). These afferent nerve discharges also variously give rise to central modulation of efferent autonomic reflexes such as for example, sympathetic activation of cardiovascular and immunological structures or parasympathetic activation of urinary tract tissues.

Sensory innervation of the carotid body via the carotid sinus branch of the glossopharyngeal nerve arises from cells within the petrosal ganglia that express high concentrations of P2X3 and P2X2 receptor subunits, giving rise to excitatory ATP gated channels of the P2X3 homotrimeric and P2X2/3 heterotrimeric forms (Prasad et al., 2001, J Physiol., 537: 667-677). Accordingly, mice engineered as deletion mutants of either P2X3 or P2X2 subunits (P2X2KO and P2X3KO mice) or cross-bred double gene-deletion mice (P2X2-P2X3dKO mice), show attenuated chemosensing responses to ATP and hypoxia, as reflected by action potential firing of the carotid sinus nerve or plethysmographically-recorded ventilatory responses (Rong et al., 2003, J. Neurosci. 23(36):11315-11321).

Without wishing to be bound by theory, medicinal agents that selectively modulate P2X3 and P2X2/3 receptors by reducing their responsiveness to the ATP released by carotid body glomus cells or other adjacent cells, or circulating in the blood are expected to reduce the level of sensory transmission to carotid sinus afferents by attenuating the ATP-dependent component, while leaving residual transmission to other non-purinergic signals intact. Thereby the pattern of persistent tonic discharge and hypersensitivity seen in pathological conditions and other untoward sympathetically driven sequelae, can be broken, thus reducing the excessive sympathetic outflow and reducing both excessive cardiac and vascular tone as well as perception of dyspnea and fatigue. Nevertheless, the presence of some signal redundancy (e.g., via ACh) will allow for the retention and preservation of important protective ventilatory reflex responses, for example in the face of significant hypoxemia.

There is evidently a need for methods of treating diseases, conditions and disorders mediated by P2X3 and/or P2X2/3 receptors, as well as a need for compounds that act as modulators of P2X receptors, including antagonists of P2X3 and P2X2/3 receptors. Such diseases and disorders are now, due to the work described herein, shown to include conditions associated with and largely resulting from enhanced sensitization of the carotid body sensing mechanism, in particular where inappropriate tonic discharge emanates within the carotid sinus nerve, as is reported to occur in many clinical conditions and as described herein.

In various aspects and embodiments, provided herein include compounds and methods for treatment of diseases driven by heightened sympathetic autonomic activity associated with P2X purinergic receptors, and more particularly to methods of using selective P2X3 and/or P2X2/3 antagonists for treatment of common signs, symptoms and morbidity of diseases in which augmented carotid body chemosensory afferent discharge and hypertonicity lead to the pathologically elevated sympathetic tone that serves as a primary driver of such disorders.

The present disclosure further provides methods for treating diseases of sympathetic nervous hyperactivity mediated by carotid body hypertonicity using a P2X3 or P2X2/3 receptor antagonist. Increased nervous activity has been shown to be directly correlated with hyperresponsiveness and tonic activity of the carotid sinus nerve in subjects, for instance in mammals such as humans or spontaneously hypertensive rats (SHRs). It can be largely corrected by antagonism of P2X3-containing receptors (e.g., P2X3 and P2X2/3). Moreover, the diaminopyrimidine antagonists exemplified herein are highly effective at attenuating both the tonic discharge of carotid sinus petrosal afferents, the sympathetic over activity to cardiovascular structures, and the consequently elevated blood pressure and ultimately associated end-organ damage. The conditions, diseases, and disorders that are associated with carotid body overactivity and tonic carotid sinus nerve discharge include, for example, hypertension, chronic sleep apnea, insulin resistance and heart failure.

Accordingly, in one aspect, the present technology may be directed to methods for treating a subject having at least one symptom of sympathetic hyperactivity and/or carotid body hypertonicity, comprising administering to a subject an effective amount of a P2X3 or P2X2/3 receptor antagonist such as a compound of formula (I). In one or more embodiments, the carotid body hypertonicity and/or sympathetic hyperactivity is modulated by a P2X3 and/or a P2X2/3 receptor antagonist. Examples of diseases driven by heightened sympathetic autonomic activity associated with P2X purinergic receptors and/or augmented carotid body chemosensory afferent discharge and hypertonicity include cardiovascular diseases and cardiopulmonary diseases as described herein. The cardiovascular disease can be driven by sympathetic hyperactivity and can be selected from chronic hypertension, (e.g., treatment-resistant hypertension), chronic heart failure, acute heart failure, arrhythmias, and stroke. The pulmonary condition can be driven by sympathetic hyperactivity and can be selected from sleep disordered breathing, and chronic obstructive sleep apnea. The pulmonary condition can also be driven by carotid body hypertonicity and can be selected from dyspnea, breathlessness, or chest tightness. In some embodiments, the pulmonary condition (e.g., chest tightness) can be associated with chronic obstructive pulmonary disease (COPD), heart failure, peripheral artery disease, idiopathic pulmonary fibrosis, or other interstitial lung disease. The metabolic condition can be driven by sympathetic hyperactivity and can be selected from diabetes mellitus and chronic kidney disease.

In another aspect, the present disclosure is directed to a method of treating carotid body hypersensitivity, hypertonicity, or clinical sequelae, in a subject by administering to such subject P2X3 or P2X2/3 receptor antagonist such as a compound of formula (I). Exemplary diseases of sympathetic nervous hyperactivity consequent to carotid body hypertonicity treatable with the invention include chronic hypertension and heart failure, where effective, safe and well-tolerated medical suppression of sympathetic overdrive have been hitherto unachievable. For example, a disease treatable by the invention is chronic treatment resistant hypertension, defined as persistent hypertension (resting office blood pressure >140/90 [SBP/DBP]) despite use of >3 antihypertensive medications including a diuretic), as well as hypertension in patients unable to tolerate currently preferred antihypertensive medications, or in whom approved medications cannot achieve recommended levels of BP control.

A disease treatable in accordance with the compositions and methods provided herein can be chronic sleep apnea, where the effect of repetitive intermittent bouts of hypoxemia and hypercapnia directly cause increased tonic discharge of the carotid body and subsequent sympathetic hyperactivity, hypertension and cardiovascular pathology.

In one or more embodiments, the methods and compositions provided herein are useful for a method for treating the signs and symptoms of carotid hypertonicity driving much of the cardiovascular morbidity associated with a cardiopulmonary disease, such as heart failure and chronic obstructive pulmonary disease, associated with pathological perception of fatigue, breathlessness, chest-tightness, dyspnea or the like.

In one or more embodiments, provided herein include a method of treatment or prevention of stroke by reducing sympathetic overactivity by a P2X3 or P2X2/3 receptor antagonist, and lessening stress on hypocompliant, inflamed and friable vascular structures.

In one or more embodiments, provided herein include methods for improving the signs and symptoms of insulin resistance, frequently associated with diabetes mellitus; and slowing the progressive deterioration in cardio-renal function in diabetic patients.

In another aspect, the administration of the compound of Formula I as defined herein can be used for treating a subject having at least one sympathetically-mediated disease.

In another aspect, administration of the compound of Formula I as defined herein can be used for suppressing the activity of the carotid body in a subject. In one or more embodiments, the compounds of Formula I can be used to treat (e.g., correct) aberrant discharge in the carotid body.

In another aspect, administration of the compound of Formula I as defined herein can be used for adjusting the autonomic balance in a subject having high sympathetic activity relative to parasympathetic activity.

In another aspect, administration of the compound of Formula I as defined herein can be used for inhibiting chemoreflex function generated by a carotid body in a subject. In one or more embodiments, inhibiting chemoreflex function generated by a carotid body in a subject can be used to treat a disease, e.g., heart failure or hypertension.

The invention also provides pharmaceutical compositions and methods of preparing the same.

As put forth herein, the present technologies feature a class of P2X3 and P2X2/3 antagonists for the treatment of diseases brought about by conditions including sympathetic nervous hyperactivity and carotid body hypertonicity. The present technology has the advantage of addressing the root cause of these illnesses instead of merely treating symptoms associated with the diseases. The technology also has the advantage of leaving the carotid body intact and allowing its normal functioning to take place. Further features and advantages are set herein and will be apparent to one of skill in the art.

Diseases or disorders treatable by the present methods include those in which the carotid body (e.g., hypertonicity or hyperactivity of the carotid body) plays a role. Exemplary diseases treatable with the invention include chronic hypertension, treatment-resistant hypertension, heart-failure, chronic obstructive sleep apnea. A condition treatable by the present methods includes chronically elevated sympathetic activity, for example in hypertension and heart failure. For example, the invention relates to a method for treating the symptoms of dyspnea, breathlessness and chest-tightness associated with a cardiopulmonary or respiratory disease. For example, the present disclosure relates to a method of treatment of the stroke and diabetes mellitus associated with a sympathetic overactivity via treatment with by a P2X3 or P2X2/3 receptor antagonist.

In certain embodiments of the present disclosure the disease to be treated or prevented may be chronic carotid body hypertonicity. For example, the invention relates to methods for reducing blood pressure in subjects with inappropriately high sympathetic tone due to excessive sensitivity of arterial chemoreceptors.

In many embodiments of the present disclosure the disorder to be treated or prevented is hypertension associated with a cardiopulmonary or cardiovascular disease.

Synthesis

Compounds of the present disclosure can be made by a variety of methods, and in some embodiments as depicted in the illustrative synthetic reaction schemes shown and described below. Syntheses of compounds for use in the invention can also be performed according to teachings presented in, for example, U.S. Pat. Nos. 8,524,725, 7,858, 632, 8,008,313; 8,003,788; 7,531,547; 7,741,484 and 7,799, 796, each of which is specifically incorporated herein in its entirety.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates a synthetic procedure usable to prepare specific compounds of formula (I) above, wherein $R^3$, $R^4$, $R^d$, and $R^e$ are as defined herein.

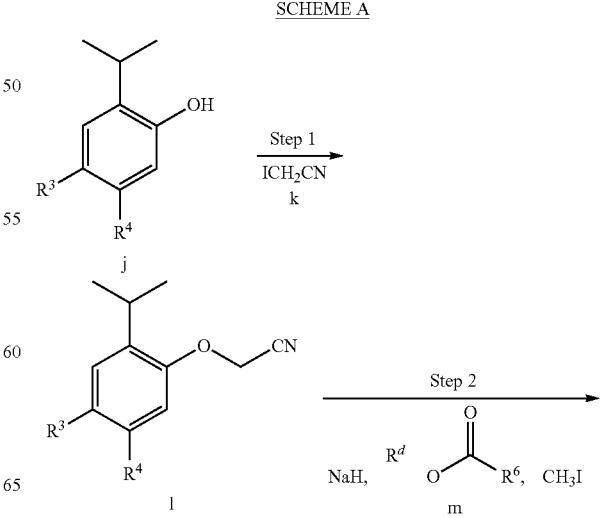

SCHEME A

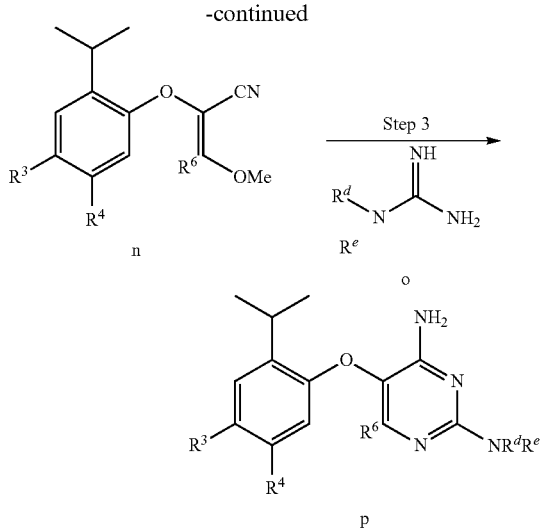

In step 1 of Scheme A, an O-alkylation is carried out by reaction of phenol i with a haloacetonitrile such as iodoacetonitrile k, to afford cyano ether l. Numerous substituted phenols i are either commercially available or may be prepared by techniques well known in the art for use in step 1. For example, substituted aldehydes may be converted to the corresponding phenols j via Baeyer-Villiger oxidation using peracid such as mCPBA, as illustrated in the experimental examples below. The alkylation of step 1 may be effected in the presence of mild base under polar aprotic solvent conditions.

In step 2, a cyano enol ether compound n is formed by treatment of cyano ether l with a strong base such as sodium hydride, followed by introduction of ester m to form an enolate (not shown), that in turn is O-alkylated by addition of iodomethane or other alkyl halide. This step may be carried out under polar aprotic solvent conditions.

In step 3 cyano enol ether n is reacted with guanidine compound o in the presence of base, under polar aprotic conditions, to yield diaminopyrimidine (p). The diaminopyrimidine (p) is a compound of formula (I) usable in the methods of the invention.

Numerous variations on the procedure of Scheme A are possible and will be readily apparent to those skilled in the art.

Specific details for producing compounds of the invention are described in the Examples below.

Use

The current technology provides compounds and methods that are useful in treating diseases in which modulation of the carotid body plays a role. For instance, the present technology provides compounds and methods to alleviate or reduce signs and/or symptoms of diseases that are caused and/or exacerbated by heightened sympathetic autonomic activity. In some preferred embodiments, the heightened sympathetic autonomic activity is associated with P2X purinergic receptors (e.g., P2X3 and/or P2X2/3 receptors), and compounds of the current invention act as antagonists to these receptors.

Exemplary diseases include cardiovascular (e.g., hypertension, heart failure, stroke,) and metabolic diseases (e.g., diabetes mellitus). Other diseases include obstructive sleep apnea and arrhythmia.

Accordingly, in some embodiments, the invention provides methods for treating a cardiovascular, cardiopulmonary or metabolic disease mediated by excessive reactivity of the carotid body and carotid sinus nerve system using an antagonist for ATP-gated receptors containing P2X3 subunits (a P2X3 and/or P2X2/3 receptor antagonist), said method comprising administering to a subject in need thereof an effective amount of a compound of formula (I).

Exemplary cardiovascular or cardiopulmonary diseases where carotid body hypertonicity and associated sympathetic overactivity can be treatable with the invention include hypertension, treatment resistant hypertension, heart failure, COPD, and chronic obstructive sleep apnea. A disease treatable by the invention includes treatment resistant hypertension, for example in subjects where the disease is either uncontrolled with existing antihypertensive options or intolerant to them.

In certain embodiments of the invention the condition treatable by the invention may be insulin resistance, such that progression of resistance towards diabetes mellitus and related diseases could be delayed or forestalled.

Certain specific examples illustrated herein demonstrate the effect of compounds of certain embodiments of the present technology on sympathetic hyperactivity using a rat model. In some embodiments, the examples set forth use Wistar rats, or spontaneously hypertensive rats (SHRs). The SHR is a well-validated model of human sympathetic over activity and the pathogenesis of hypertension. As with humans, the SHR develops a hypersensitive and hypertrophic carotid body that precedes the development of sympathoexcitation and hypertension. Accordingly, a skilled artisan will understand that the Wistar and SHR model is appropriate for elucidating the effect of compounds of the present invention in a mammalian subject, such as a human patient. See, e.g., Paton et al., *Curr Hypertens Rep* (2013) 15:273-280.

FIGS. 1A-1D show the effects of Compound A, a benzyl-diaminopyrimidine P2X3 antagonist which is seen to reduce carotid sinus nerve activity and excitatory responses to hypoxia and ATP (or analogs), in an isolated preparation of carotid body/carotid sinus nerves. FIG. 1A shows this effect in a wild-type mouse P2X2-P2X2/3 carotid/sinus nerve preparation. As shown, the dual P2X3 and P2X2/3 antagonist Compound A attenuates basal tonic firing and hypoxia-induced excitation of carotid sinus afferents in an isolated carotid body preparation of mouse. In wild type preparations, Compound A reversibly inhibits the response of sinus nerve hypoxia. The IC$_{50}$ is in the range between 10-30 µM.

Figure 1B:
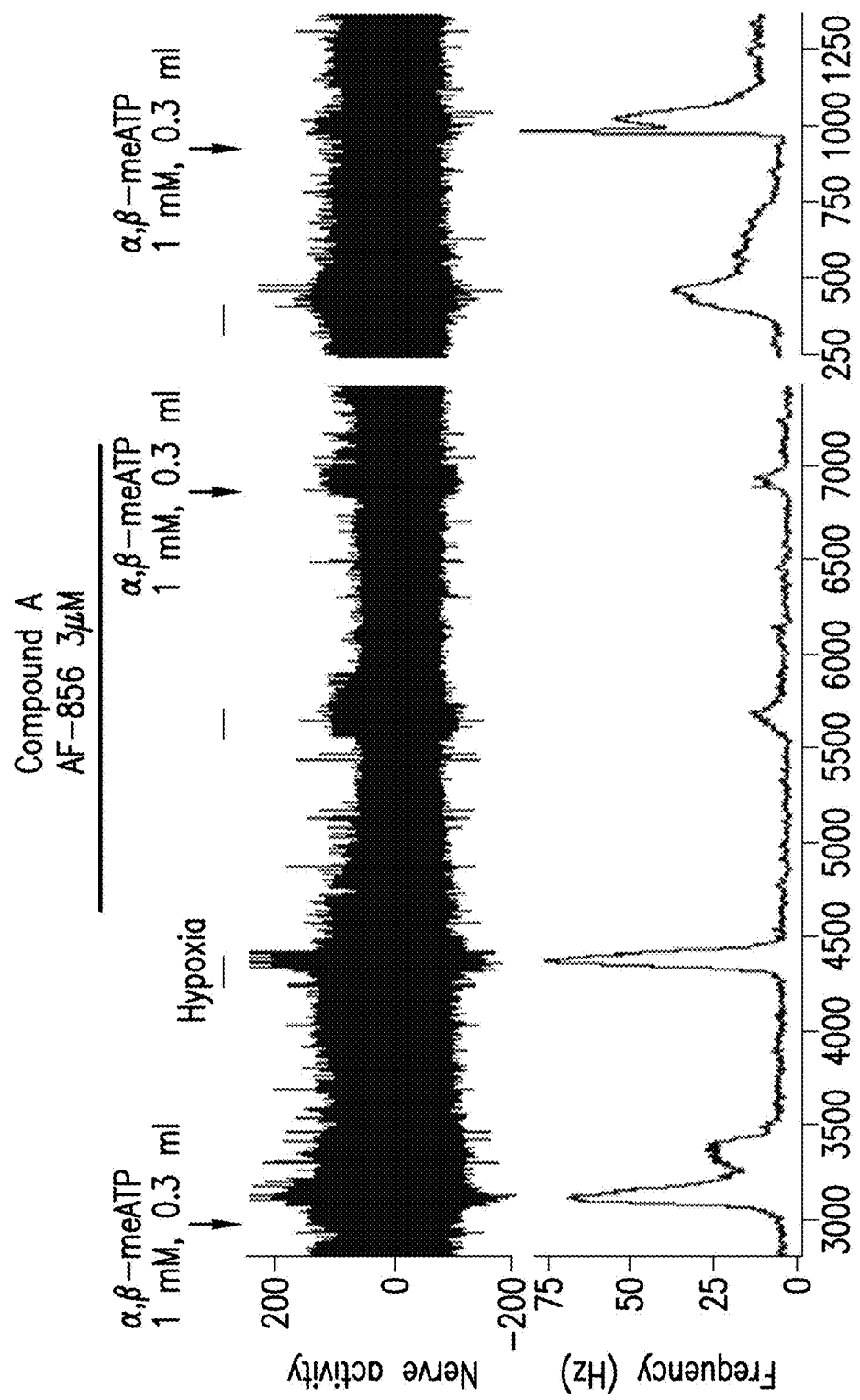

FIG. 1B shows the effects of Compound A on homotrimeric P2X3 mediated responses of the sinus nerve to α,β-MeATP and hypoxia in P2X2 KO mice. FIG. 1B demonstrates that the dual P2X3 and P2X2/3 antagonist Compound A attenuates basal tonic firing and hypoxia, as well as α,β-MeATP induced excitation of carotid sinus afferents in an isolated carotid body preparation of P2X2 KO mouse. Greater potency is shown by effectiveness of lower concentrations of Compound A, consistent with the dominant role of P2X3 homotrimers in the carotid sinus response in the absence of P2X2 subunits.

Figure 1C:
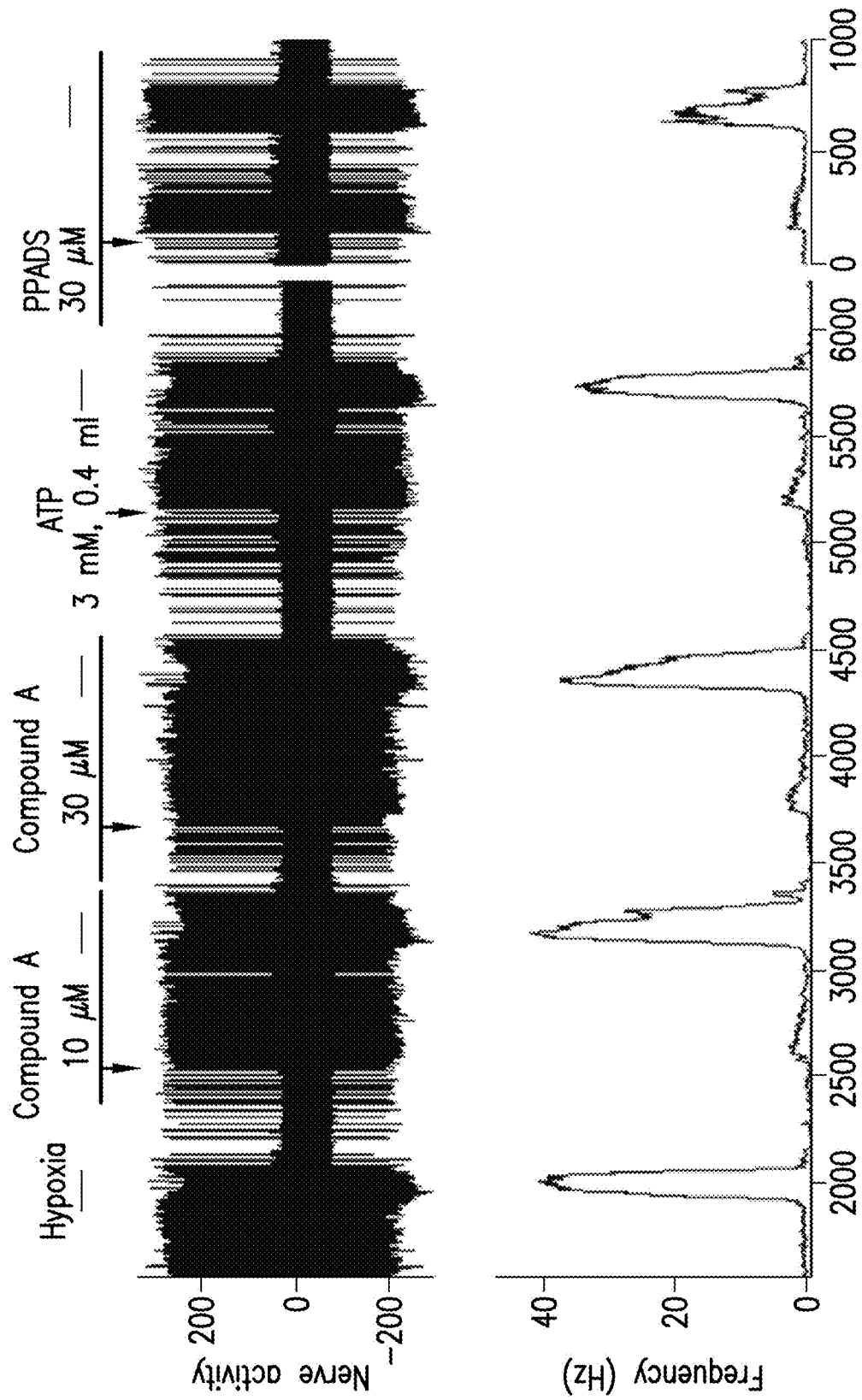
FIG. 1C shows the effects of Compound A on carotid sinus nerve activity and excitatory responses to hypoxia and ATP (or analogs) in a P2X3-gene deletion mutant (P2X3KO) mouse.

FIG. 1C shows the effects of Compound A on homotrimeric P2X2 mediated responses of the sinus nerve to α,β-MeATP and hypoxia in P2X3 KO mice. FIG. 1C shows that the dual P2X2 and P2X2/3 antagonist Compound A fails to attenuate basal tonic firing and hypoxia or ATP-induced excitation of carotid sinus afferents in an isolated carotid body preparation of the P2X3 KO mouse. The non-selective antagonist PPADS did show inhibitory activity. FIGS. 2A-D show the results of studies on the effects of P2X3 and P2X2/3 antagonism on carotid body responses, carotid body hypertonicity, sympathetic discharge and blood pressure in spontaneously hypertensive rats.

Figure 2A:
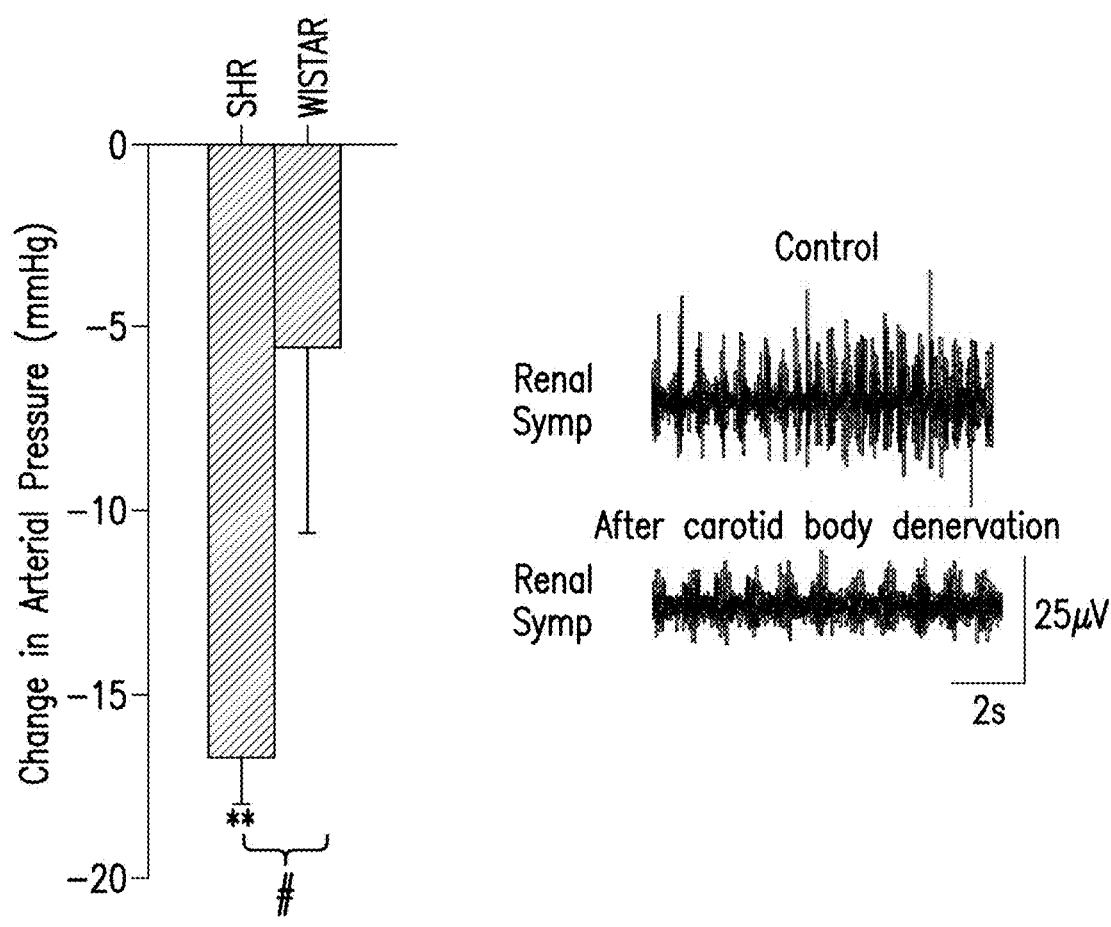
FIG. 2A shows denervation of the carotid body chemosensors in conscious SHRs (compared with normotensive Wistar rats) markedly reduces arterial blood pressure and renal sympathetic nerve activity.

FIG. 2A shows that in conscious, unrestrained spontaneously hypertensive rats, denervation of the carotid bodies bilaterally lowered both arterial pressure and renal sympathetic nerve activity (~55%), an effect not seen in normotensive Wistar rats (McBryde et al, 2013). These data led to the hypothesis that there is aberrant carotid body activity in SHR that drives sympathetic activity. The term "renal symp" is understood to mean sympathetic nerve activity to the kidney.

Figure 2B:
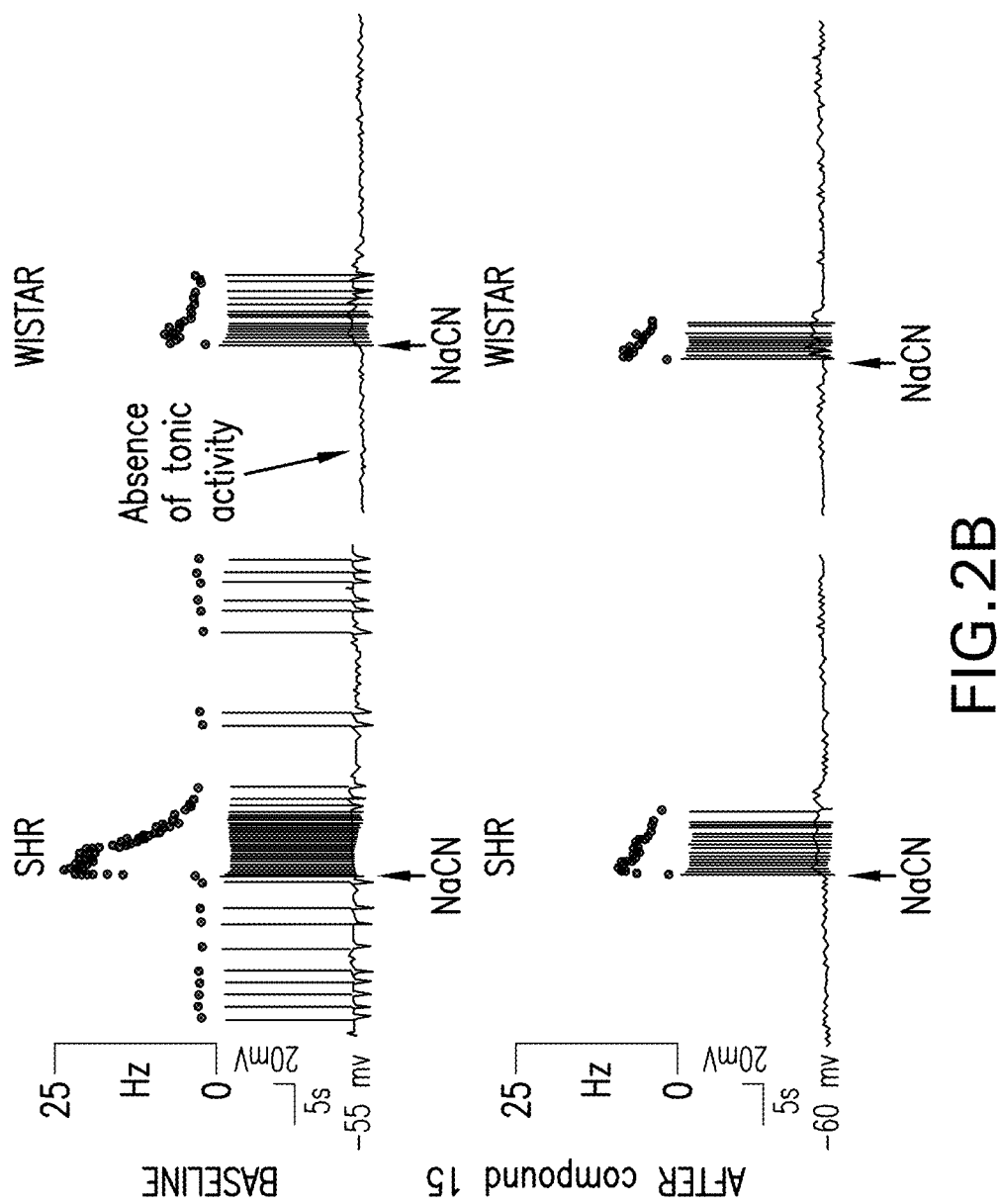
FIG. 2B SHRs show characteristic tonic activity in petrosal ganglion neuronal cell bodies of carotid sinus afferents, as well as exaggerated responses to chemical provocation with NaCN, that are absent or lessened in Wistar rats.

FIG. 2B shows that spontaneously hypertensive rats show tonicity (aberrant discharge), depolarized membrane potential and exaggerated firing responses to chemoreceptor stimuli. There is an absence of tonic activity in normotensive Wistar rats. Both the tonic activity in SHRs and the exaggerated chemical responses are markedly attenuated by a compound of formula (I), whereas Wistar rats are less affected. Blockade of P2X3 receptors in the carotid body with a compound of formula (I) abolished tonic activity and suppressed peripheral chemoreceptor reflex evoke firing response in petrosal neurons in spontaneously hypertensive rats.

Figure 2C:
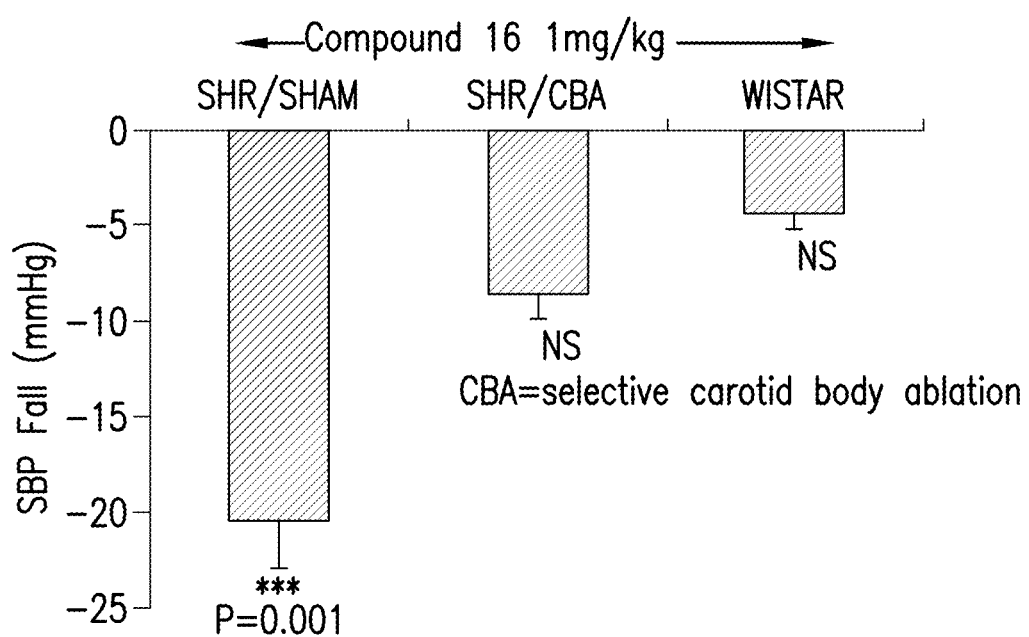
FIG. 2C shows that significant reductions in arterial blood pressure in SHRs are seen following bolus dosing of a Compound of formula I (1 mg/kg), which are absent in SHRs following carotid body ablation as well as in normotensive Wistar rats.
Figure 2D:
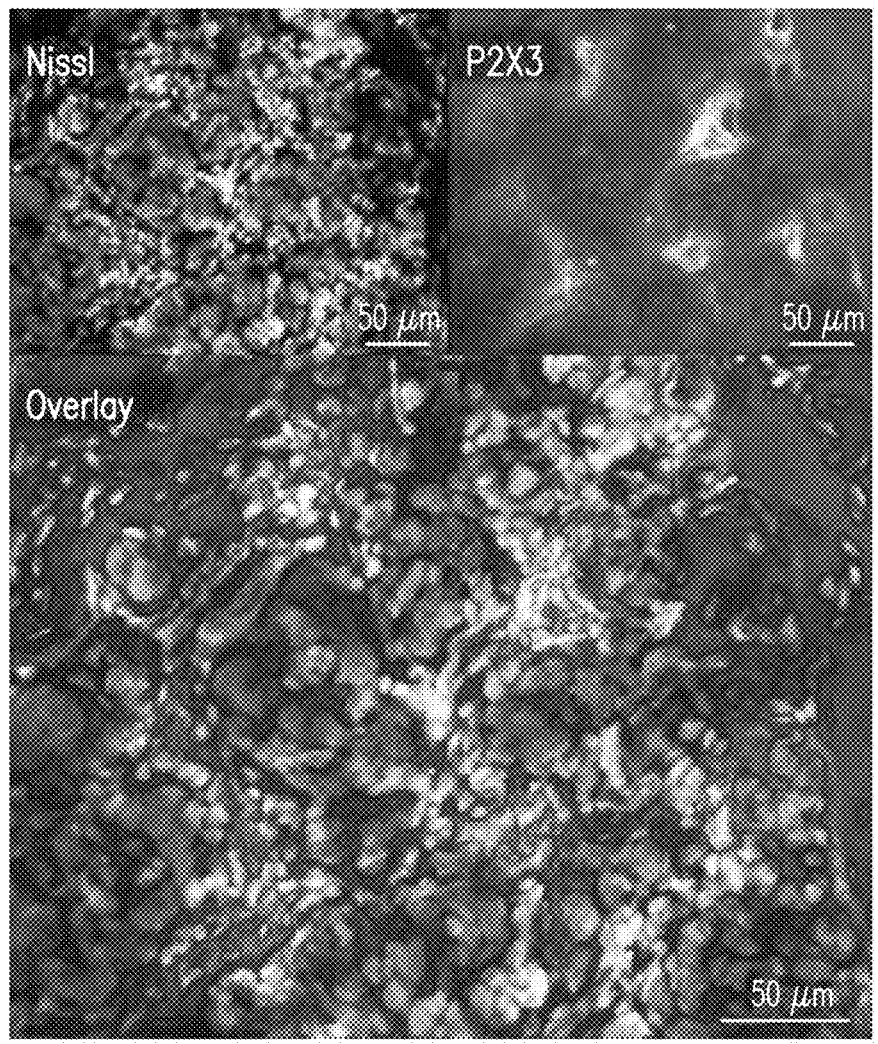
FIG. 2D illustrates immunocytochemical labelling of a section of carotid body from a hypertensive human subject.

FIG. 2C shows the anti-hypertensive action of P2X3 receptor antagonism (bolus i.v.) in conscious, radio-telemetered spontaneously hypertensive rats is dependent on the integrity of carotid body chemoreceptors. There was no significant change in arterial pressure following P2X3 antagonism in normotensive Wistar rats (Pijacka, Ford & Paton, unpublished data). FIG. 2D shows immunocytochemical staining for P2X3 receptors in the carotid body of a hypertensive human subject. *Glomus* cells are labelled with Nissl stain. The pattern of the P2X3 immunofluorescence resembles that of fiber bundles innervating clusters of *glomus* cells. This confirms the expression of P2X3 and/or P2X2/3 receptors on target sensory neurons.

In one or more embodiments, the present technology provides methods for treating a respiratory disease mediated by a P2X3 or P2X2/3 receptor antagonist, the method comprising administering a compound of Formula I. Exemplary respiratory diseases include, but are not limited to chronic obstructive pulmonary disease (COPD), asthma, bronchospasm, and the like.

In another embodiment, the present technology provides methods for treating a subject suffering from a sympathetically-mediated disease comprising administering a compound of Formula I. Exemplary sympathetically-mediated diseases include, but are not limited to elevated sympathetic tone, an elevated sympathetic/parasympathetic activity ratio, autonomic imbalance primarily attributable to central sympathetic tone being abnormally high, or heightened sympathetic tone at least partially attributable to afferent excitation traceable to hypersensitivity or hyperactivity of a peripheral chemoreceptor (e.g., carotid body). Other sympathetically mediated diseases include cardiac, metabolic, or pulmonary disease such as hypertension (e.g., refractory hypertension), congestive heart failure (CHF), diabetes, period breathing, insulin resistance, heart failure, or dyspnea. In some embodiments, the hypertension is drug resistant hypertension, or hypertension resistant to renal denervation. In one or more embodiments, the present technology provides methods for suppressing the activity of the carotid body in a subject.

In one or more embodiments, the present technology provides methods for adjusting the autonomic balance in a subject having high sympathetic activity relative to parasympathetic activity comprising administering a compound of Formula I. In some embodiments, this includes reducing sympathetic activity. In one or more embodiments, the present technology provides methods for inhibiting chemoreflex function generated by a carotid body comprising administering a compound of Formula I.

In one or more embodiments, compounds of the current disclosure can be used to inhibit the response of the sinus nerve in a subject to hypoxia. In some embodiments, the effect is dose-dependent. The response can also be reversible. In some embodiments, the $IC_{50}$ range is between about 1 and 30 µm; about 10 and 30 µm; or between about 1 and 10 µm; or between about 1 and 1000 nm, or between about 1 and 100 nm; or between about 100 and 500 nm; or between about 500 and 1000 nm.

In some embodiments, compounds of the present disclosure can inhibit the response to α,β-meATP and hypoxia mediated by homomeric P2X3 receptors.

In some embodiments, compounds of the present disclosure can block ATP response in the sinus nerve of a subject (e.g., a human, or, for example, a model of a human disease or disorder such as a P2X2 knockout mouse). In some embodiments, the effect is reversible. In some embodiments, compounds of the present disclosure can reversibly block homomeric P2X3-mediated response of the sinus nerve to hypoxia.

In one or more embodiments, compounds of the present disclosure are selective antagonists of homomeric P2X3 and P2X2/3 receptors (e.g., human or mouse homomeric P2X3 and P2X2/3 receptors). The $IC_{50}$ values for P2X3 inhibition can be about 3 µm (e.g., less than 3 µm). The $IC_{50}$ values for P2X2/3 can be about 15 µm (e.g., less than 15 µm). In some embodiments, compounds of the present disclosure are more potent against P2X3 than against P2X2/3 (e.g., 5× more potent, 10× more potent, 20× more potent, or 100× more potent). In some embodiments, the $IC_{50}$ range is between about 1 and 30 µm; about 10 and 30 µm; or between about 1 and 10 µm; or between about 1 and 1000 nm, or between about 1 and 100 nm; or between about 100 and 500 nm; or between about 500 and 1000 nm.

In some embodiments, use of the compounds of the present disclosure to antagonize P2X3 can abolish carotid chemoreceptor tone but not reflex response. Compounds of the present disclosure in various aspects and embodiments disclosed herein can reduce the intrinsic excitability of carotid body petrosal cells in a subject (e.g., mammals including rodents such as rats or mice, and primates such as apes or humans). In some embodiments, the subjects (e.g., rats) are in a hyperoxic condition.

Compounds of the present disclosure can decrease baseline and chemoreflex-induced sympathoexcitation in a subject (e.g., human or a human model such as SH rats). In some embodiments, the subjects (e.g., humans or rats) are in a hyperoxemic or hypoxemic condition.

In some embodiments, the lowering of blood pressure mediated by P2X3 receptor antagonism is dependent upon the carotid body. In some embodiments, the lowering of blood pressure takes place in a subject (e.g., a human or a rat).

Administration and Pharmaceutical Composition

The disclosure includes pharmaceutical compositions comprising at least one compound of the present disclosure, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the disclosure will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present disclosure for a given disease.

Compounds of the disclosure may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the disclosure, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the disclosure may be formulated in a wide variety of oral administration dosage forms. The pharmaceutical compositions and dosage forms may comprise a compound or compounds of the present disclosure or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the disclosure may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the subject administering an appropriate, predetermined volume of the solution or suspension. In the case of a spray, this may be achieved for example by means of a metering atomizing spray pump.

The compounds of the disclosure may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present disclosure can be formulated in transdermal or subcutaneous drug delivery devices. These delivery systems are advantageous when sustained release of the compound is necessary and when subject compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Exemplary pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound may in some embodiments be prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Other suitable pharmaceutical carriers and their formulations are described in *Remington: The Science and Practice of Pharmacy* 1995, edited by E. W. Martin, Mack Publishing Company, 19th edition, Easton, Pa.

Non-Limiting List of Exemplary Embodiments

In addition to the aspects and embodiments described and provided elsewhere in this disclosure, the following non-limiting list of particular embodiments are specifically contemplated:

1. A method of treating hypertension in a subject, comprising identifying a subject diagnosed with hypertension and administering to the subject a compound of formula (I).
2. A method of treating heart failure in a subject, comprising identifying a subject diagnosed with heart failure and administering to the subject a compound of formula (I).
3. A method of treating dyspnea in a subject, comprising identifying a subject diagnosed with dyspnea and administering to the subject a compound of formula (I).
4. A method of treating sleep apnea in a subject, comprising identifying a subject diagnosed with sleep apnea and administering to the subject a compound of formula (I).
5. A method for altering carotid body tonicity or activity in a subject, involving identifying a subject in need of altering carotid body tonicity or activity and administering to the subject a compound of formula (I).
6. A method for reducing carotid body tonicity in a subject, comprising identifying a subject in need of reduction in carotid body tonicity or activity and administering to the subject a compound of formula (I).
7. A method of reducing carotid body chemosensory afferent discharge in a subject, comprising identifying a subject in need of reduction in carotid body chemosensory afferent discharge and administering to the subject a compound of formula (I).
8. A method of treating a subject having at least one symptom of sympathetic hyperactivity or carotid body hypertonicity, said method comprising identifying a subject having at least one symptom of sympathetic hyperactivity or carotid body hypertonicity and administering to said subject an effective amount of a compound of Formula (I); wherein the carotid body hypertonicity or sympathetic hyperactivity is optionally associated with cardiopulmonary, cardiovascular, or metabolic disease.
9. A method of treating carotid body hypersensitivity, hypertonicity, or clinical sequelae, in a subject, comprising identifying a subject in need of carotid body hypersensitivity, hypertonicity, or clinical sequelae treatment and administering to said subject a compound of formula (1).
10. A method of suppressing the activity of the carotid body in a subject, comprising identifying a subject in need of carotid body activity suppression and administering to said subject a compound of formula (1).
11. A method of adjusting the autonomic balance in a subject having high sympathetic activity relating to parasympathetic activity, comprising identifying an individual having high sympathetic activity relating to parasympathetic activity, and administering to said subject a compound of formula (I).
12. The method of any of the preceding embodiments wherein the compound of formula (I) has below formula (I):

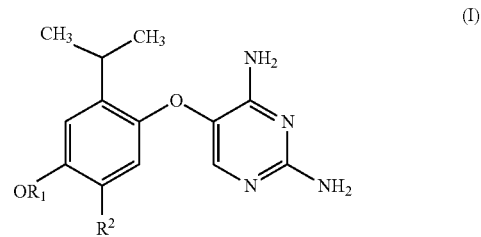

(I)

or a pharmaceutically acceptable salt thereof; wherein $R^1$ is hydrogen or optionally substituted $C_1$-$C_6$ alkyl; and $R^2$ is alkyl; alkenyl; alkynyl; amino; aminosulfonyl; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; carboxyalkyl; cyano or alkylcarbonyl.

13. The method of any of the preceding embodiments, wherein $R^2$ of the compound of formula (I) is haloalkyl, aminosulfonyl, alkylsulfonyl alkylcarbonyl or carboxyalkyl.
14. The method of any of the preceding embodiments, wherein $R^2$ of the compound of formula (I) is haloalkyl, and wherein the alkyl is methyl.
15. The method of any of the preceding embodiments, wherein the compound of formula (I) is selected from the group consisting of compounds of Table 1.
16. The method of any of the preceding embodiments, wherein the compound of formula (I) is Compound #1 on Table 1.
17. The method of any of the preceding embodiments, wherein the compound of formula (I) is Compound #2 on Table 1.
18. The method of any of the preceding embodiments, wherein the compound of formula (I) is Compound #3 on Table 1.
19. The method of any of the preceding embodiments, wherein the compound of formula (I) is Compound #4 on Table 1.
20. The method of any of the preceding embodiments, wherein the compound of formula (I) is Compound #5 on Table 1.
21. The method of any of the preceding embodiments, wherein the compound of formula (I) is Compound #6 on Table 1.
22. The method of any of the preceding embodiments, wherein the compound of formula (I) is Compound #7 on Table 1.

23. The method of any of the preceding embodiments, wherein the compound of formula (I) is Compound #8 on Table 1.
24. The method of any of the preceding embodiments, wherein the compound of formula (I) is Compound #9 on Table 1.
25. The method of any of the preceding embodiments, wherein the compound of formula (I) is Compound #10 on Table 1.
26. The method of any of the preceding embodiments, wherein the compound of formula (I) is Compound #11 on Table 1.
27. The method of any of the preceding embodiments, wherein the compound of formula (I) is Compound #12 on Table 1.
28. The method of any of the preceding embodiments, wherein the compound of formula (I) is Compound #13 on Table 1.
29. The method of any of the preceding embodiments, wherein the compound of formula (I) is Compound #14 on Table 1.
30. The method of any of the preceding embodiments, wherein the compound of formula (I) is Compound #15 on Table 1.
31. The method of any of the preceding embodiments, wherein the compound of formula (I) is Compound #16 on Table 1.
32. The method of any of the preceding embodiments, wherein the compound of formula (I) is Compound #17 on Table 1.
33. The method of any of the preceding embodiments, wherein the compound of formula (I) is Compound #18 on Table 1.
34. The method of any of the preceding embodiments, wherein the compound of formula (I) is Compound #19 on Table 1.
35. The method of any of the preceding embodiments, wherein the compound of formula (I) is Compound #20 on Table 1.
36. The method of any of the preceding embodiments, wherein the compound of formula (I) is Compound #21 on Table 1.
37. The method of any of the preceding embodiments, wherein the compound of formula (I) is Compound #22 on Table 1.
38. The method of any of the preceding embodiments, wherein the compound of formula (I) is Compound #23 on Table 1.
39. The method of any of the preceding embodiments, wherein the compound of formula (I) is Compound #24 on Table 1.
40. The method of any of the preceding embodiments, wherein the compound of formula (I) is Compound #25 on Table 1.
41. The method of any of the preceding embodiments, wherein the compound of formula (I) is Compound #26 on Table 1.
42. The method of any of the preceding embodiments, wherein the compound of formula (I) is Compound #27 on Table 1.
43. The method of any of the preceding embodiments, wherein the compound of formula (I) is Compound #28 on Table 1.
44. The method of any of the preceding embodiments, wherein the compound of formula (I) is Compound #29 on Table 1.
45. The method of any of the preceding embodiments, wherein the compound of formula (I) is Compound #30 on Table 1.
46. The method of any of the preceding embodiments, wherein the compound of formula (I) is Compound #31 on Table 1.
47. The method of any of the preceding embodiments, wherein the compound of formula (I) is Compound #32 on Table 1.
48. The method of any of the preceding embodiments, wherein the compound of formula (I) is Compound #33 on Table 1.
49. The method of any of the preceding embodiments, wherein the compound of formula (I) is Compound #34 on Table 1.
50. The method of any of the preceding embodiments, wherein the compound of formula (I) is Compound #35 on Table 1.
51. The method of any of the preceding embodiments, wherein the compound of formula (I) is Compound #36 on Table 1.
52. The method of any of the preceding embodiments, wherein the compound of formula (I) is Compound #37 on Table 1.
53. A method of treating hypertension in a subject, comprising identifying a subject diagnosed with hypertension and administering to the subject a compound of formula (I).
54. A method of treating heart failure in a subject, comprising identifying a subject diagnosed with heart failure and administering to the subject a P2X3 and/or a P2X2/3 receptor antagonist.
55. A method of treating dyspnea in a subject, comprising identifying a subject diagnosed with dyspnea and administering to the subject a P2X3 and/or a P2X2/3 receptor antagonist.
56. A method of treating sleep apnea in a subject, comprising identifying a subject diagnosed with sleep apnea and administering to the subject a P2X3 and/or a P2X2/3 receptor antagonist.
57. A method for altering carotid body tonicity or activity in a subject, involving identifying a subject in need of altering carotid body tonicity or activity and administering to the subject a P2X3 and/or a P2X2/3 receptor antagonist.
58. A method for reducing carotid body tonicity in a subject, comprising identifying a subject in need of reduction in carotid body tonicity or activity and administering to the subject a P2X3 and/or a P2X2/3 receptor antagonist.
59. A method of reducing carotid body chemosensory afferent discharge in a subject, comprising identifying a subject in need of reduction in carotid body chemosensory afferent discharge and administering to the subject a P2X3 and/or a P2X2/3 receptor antagonist.
60. A method of treating a subject having at least one symptom of sympathetic hyperactivity or carotid body hypertonicity, said method comprising identifying a subject having at least one symptom of sympathetic hyperactivity or carotid body hypertonicity and administering to said subject an effective amount of a P2X3 and/or a P2X2/3 receptor antagonist; wherein the carotid body hypertonicity or sympathetic hyperactivity is optionally associated with cardiopulmonary, cardiovascular, or metabolic disease.
61. A method of treating carotid body hypersensitivity, hypertonicity, or clinical sequelae, in a subject, comprising identifying a subject in need of carotid body hypersensitivity, hypertonicity, or clinical sequelae treatment and administering to said subject a P2X3 and/or a P2X2/3 receptor antagonist.

62. A method of suppressing the activity of the carotid body in a subject, comprising identifying a subject in need of carotid body activity suppression and administering to said subject a P2X3 and/or a P2X2/3 receptor antagonist.

63. A method of adjusting the autonomic balance in a subject having high sympathetic activity relating to parasympathetic activity, comprising identifying an individual having high sympathetic activity relating to parasympathetic activity, and administering to said subject a P2X3 and/or a P2X2/3 receptor antagonist.

64. The method of any of the preceding embodiments, wherein a subject diagnosed with hypertension, if present, has a systolic blood pressure above about 120 mmHg and/or a diastolic pressure above about 80 mmHg.

65. The method of any of the preceding embodiments, wherein a subject diagnosed with hypertension, if present, has a systolic blood pressure above about 125 mmHg.

66. The method of any of the preceding embodiments, wherein a subject diagnosed with hypertension, if present, has a systolic blood pressure above about 130 mmHg.

67. The method of any of the preceding embodiments, wherein a subject diagnosed with hypertension, if present, has a systolic blood pressure above about 140 mmHg.

68. The method of any of the preceding embodiments, wherein a subject diagnosed with hypertension, if present, has a systolic blood pressure above about 150 mmHg.

69. The method of any of the preceding embodiments, wherein a subject diagnosed with hypertension, if present, has a systolic blood pressure above about 160 mmHg.

70. The method of any of the preceding embodiments, wherein a subject diagnosed with hypertension, if present, has a diastolic pressure above about 85 mmHg.

71. The method of any of the preceding embodiments, wherein a subject diagnosed with hypertension, if present, has a diastolic pressure above about 90 mmHg.

72. The method of any of the preceding embodiments, wherein a subject diagnosed with hypertension, if present, has a diastolic pressure above about 95 mmHg.

73. The method of any of the preceding embodiments, wherein a subject diagnosed with hypertension, if present, has a diastolic pressure above about 100 mmHg.

74. The method of any of the preceding embodiments, wherein a subject diagnosed with hypertension, if present, is diagnosed with chronic treatment resistant hypertension.

75. The method of any of the preceding embodiments, wherein said subject diagnosed with heart failure, if present, is diagnosed with systolic heart failure.

76. The method of any of the preceding embodiments, wherein said subject diagnosed with heart failure, if present, is diagnosed with diastolic heart failure.

77. The method of any of the preceding embodiments, wherein said subject diagnosed with heart failure, if present, is diagnosed with chronic heart failure.

78. The method of any of the preceding embodiments, wherein said subject diagnosed with heart failure, if present, is diagnosed with acute heart failure.

79. The method of any of the preceding embodiments, wherein said subject diagnosed with sleep apnea, if present, is diagnosed with central sleep apnea.

80. The method of any of the preceding embodiments, wherein said subject diagnosed with sleep apnea, if present, is diagnosed with obstructive sleep apnea.

81. The method of any of the preceding embodiments, wherein said subject diagnosed with sleep apnea, if present, is diagnosed with mixed sleep apnea.

82. The method of any of the preceding embodiments, wherein said subject diagnosed with sleep apnea, if present, is diagnosed as having more than about 5 apneic events per hour of sleep.

83. The method of any of the preceding embodiments, wherein said subject diagnosed with sleep apnea, if present, is diagnosed as having more than about 15 apneic events per hour of sleep.

84. The method of any of the preceding embodiments, wherein said subject diagnosed with sleep apnea, if present, is diagnosed as having more than about 25 apneic events per hour of sleep.

EXAMPLES

The following preparations and examples are given to enable those skilled in the art to more clearly understand and to practice certain technologies, methods, inventions, compositions, concepts disclosed herein. They should not be considered as limiting the scope of any inventions, but merely as being illustrative and representative thereof.

Example 1

5-(5-Bromo-2-isopropyl-4-methoxy-phenoxy)-pyrimidine-2,4-diamine

The synthetic procedure used in this Example is outlined in Scheme B.

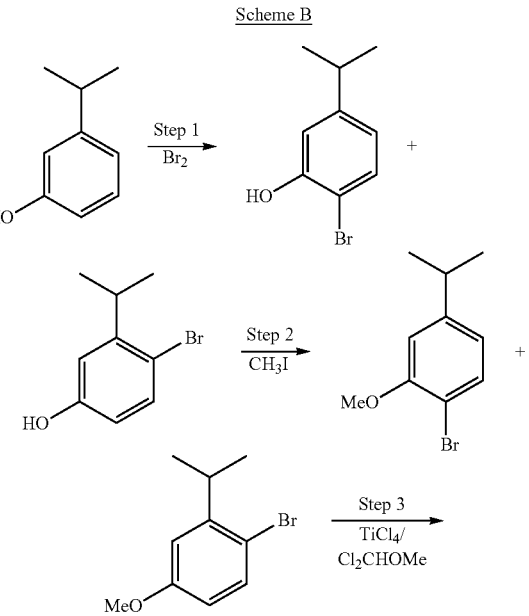

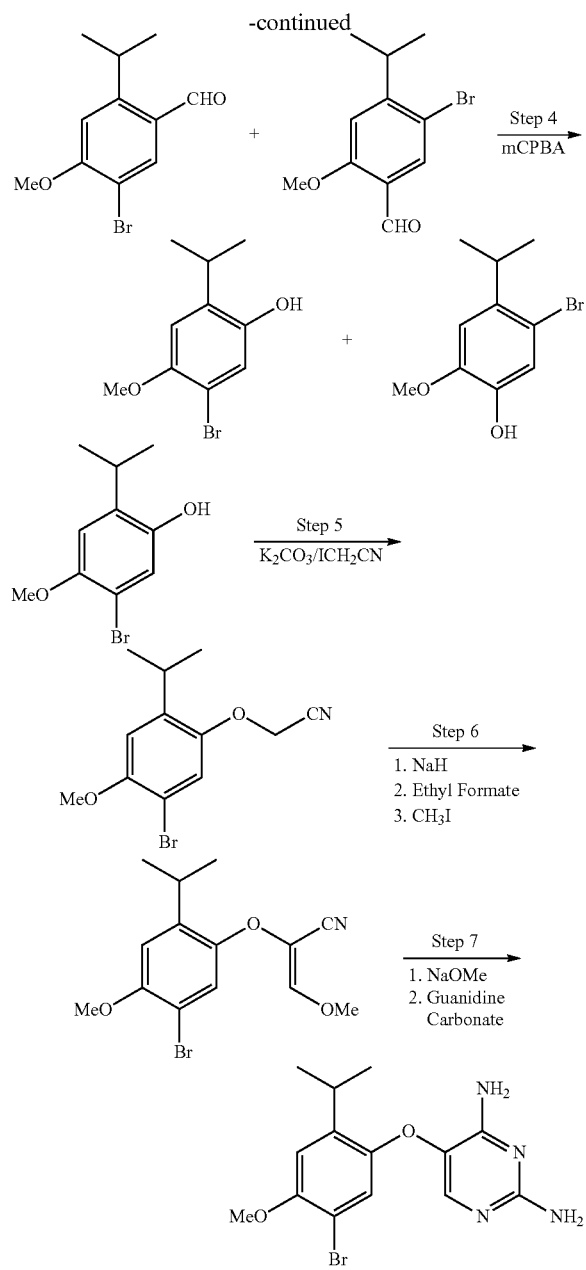

mmol), K₂CO₃ (16.710 g, 120.9 mmol) in 50 mL DMF, was added iodomethane (3.0 mL, 48.3 mmol) with mechanical stirring. The mixture was warmed to 50° C. for 4 hours. After cooling to room temperature 300 mL H₂O was added and the solution was extracted with diethyl ether (Et₂O), washed with H₂O and washed with brine. The combined organics were dried over MgSO₄, filtered and concentrated in vacuo to give 1-bromo-4-isopropyl-2-methoxy-benzene and 1-bromo-2-isopropyl-4-methoxy-benzene (6.621 g, 72%) as a 1:1 inseparable mixture in the form of a pale yellow oil. This mixture of regioisomers was used directly in step 3 below.

Step 3.
5-Bromo-2-isopropyl-4-methoxy-benzaldehyde

To a solution of 1-bromo-4-isopropyl-2-methoxy-benzene and 1-bromo-2-isopropyl-4-methoxy-benzene from step 2 (6.621 g, 28.9 mmol) in 100 mL 1,2 dichloroethane was added TiCl₄ (6.3 mL, 57.8 mmol) at 0° C. After 10 minutes, dichloromethoxymethane (Cl₂CHOMe) (2.6 mL, 28.9 mmol) was added and the mixture was warmed to reflux. After 3 hours the mixture was cooled poured over ice and acidified with 50 mL 2 M HCl. The resulting slurry was extracted with CH₂Cl₂, and washed with brine. The combined organics were dried over MgSO₄, filtered and concentrated in vacuo to give a dark-green oil. Purification via flash chromatography (96:4 hexane/ethyl acetate) afforded 5-bromo-2-isopropyl-4-methoxy-benzaldehyde and 5-bromo-4-isopropyl-2-methoxy-benzaldehyde (2.876 g, 39%, 6.621 g, 72%) as a 1:1 mixture of inseparable isomers in the form of an orange oil, which was used directly in step 4.

Step 4. 5-Bromo-2-isopropyl-4-methoxy-phenol

To a solution of 5-bromo-2-isopropyl-4-methoxy-benzaldehyde and 5-bromo-4-isopropyl-2-methoxy-benzaldehyde from step 3 (2.87 g, 11.2 mmol) in 25 mL CH₂Cl₂ was added mCPBA (2.31 g, 13.4 mmol). After 16 hours the mixture was taken up in 150 ml CH₂Cl₂ and washed with sat NaHCO₃, and then with brine. The combined organic layers were dried over Na₂SO₄, filtered and concentrated in vacuo to give an oil that was taken up in 50 mL MeOH and 30 mL 4M NaOH. After 2 hours the mixture was evaporated, diluted with water and acidified to pH=1 with concentrated HCl. The mixture was extracted with ethyl acetate (3×100 mL) and washed with 100 mL brine. The combined organics were dried over Na₂SO₄, filtered and evaporated to give a mixture of 5-bromo-2-isopropyl-4-methoxy-phenol and 2-bromo-5-isopropyl-4-methoxy-phenol as an orange residue. These regioisomers were separable by flash chromatography (gradient: hexane, 7:3, 1:1 hexane/CH₂Cl₂) to afford 5-bromo-2-isopropyl-4-methoxy-phenol (0.929, 34%) as a yellow oil which was used in the following step, and 2-bromo-5-isopropyl-4-methoxy-phenol (0.404 g, 15%) as a yellow solid.

Step 5. (5-Bromo-2-isopropyl-4-methoxy-phenoxy)-acetonitrile

To a mixture of 5-bromo-2-isopropyl-4-methoxy-phenol from step 4 (0.831 g, 3.4 mmol) and K₂CO₃ (0.562 g, 4.1 mmol) in 17 mL dimethyl formamide (DMF) was added iodoacetonitrile (0.594 g, 3.6 mmol). The mixture was warmed to 60° C. for 30 minutes and then allowed to cool to room temperature. After cooling to room temperature the Step 1. 2-Bromo-5-isopropyl-phenol A solution of 3-isopropyl phenol (4.975 g, 36.5 mmol) in 37 mL of CCl₄ was cooled to −20° C. Bromine (1.9 mL, 38.4 mmol) was dissolved in 5.0 mL CCl₄ and added drop-wise at such a rate that the internal temperature was maintained below −10° C. The mixture was allowed to warm to room temperature. After 12 hours the mixture was taken up in 100 mL CH₂Cl₂, washed with H₂O and then with brine. The combined organics were dried over Na₂SO₄, filtered and concentrated in vacuo to give 8.663 g of a 1:1 mixture of 2-bromo-5-isopropyl-phenol and 4-bromo-5-isopropyl phenol as a dark oil). These two isomers were inseparable and were used together in step 2 below.

Step 2. 1-Bromo-4-isopropyl-2-methoxy-benzene

To a mixture of 2-bromo-5-isopropyl-phenol and 4-bromo-5-isopropyl phenol from step 1 (8.663 g, 40.3 mixture was taken up in 50 mL of H$_2$O and extracted with 1:1 toluene/ethyl acetate, washed with H$_2$O and then with brine. The combined organic layers were dried over Na$_2$SO$_4$, filtered and concentrated in vacuo to give a crude solid. Purification via flash chromatography (1:1 hexane/CH$_2$Cl$_2$) afforded (5-bromo-2-isopropyl-4-methoxy-phenoxy)-acetonitrile (0.611 g, 63%) as a while solid.

Step 6. 2-(5-Bromo-2-isopropyl-4-methoxy-phenoxy)-3-methoxy-acrylonitrile

Sodium hydride (0.122 g, 5.0 mmol, 60% w/w) was washed with dry hexanes and evaporated under a stream of nitrogen. 10 mL THF was added and the mixture was cooled to 0° C. (5-Bromo-2-isopropyl-4-methoxy-phenoxy)-acetonitrile (0.577 g, 2.03 mmol) was added in portions. After 30 min ethyl formate (4.9 mL, 60.9 mmol) was added and the solution was warmed to 80° C. After 4.5 hours the mixture was cooled and 5.0 mL iodomethane was added in one portion. After 16 hours the solution was quenched with H$_2$O, concentrated in vacuo, extracted with ethyl acetate, washed with H$_2$O and then washed with brine. The combined organic layers were dried over Na$_2$SO$_4$, filtered and concentrated in vacuo. Purification via flash chromatography (9:1 hexane/ethyl acetate) afforded 2-(5-bromo-2-isopropyl-4-methoxy-phenoxy)-3-methoxy-acrylonitrile (0.319 g, 48%) as a white solid.

Step 7. 5-(5-Bromo-2-isopropyl-4-methoxy-phenoxy)-pyrimidine-2,4-diamine

To a solution of 2-(5-bromo-2-isopropyl-4-methoxy-phenoxy)-3-methoxy-acrylonitrile (0.282 g, 0.9 mmol) and guanidine carbonate (0.078 g, 0.4 mmol) in 10.0 mL dimethyl sulfoxide (DMSO) was added sodium methoxide (1.0 mL, 1.0M in MeOH). The mixture was warmed to 120° C. The methanol was collected via a short-path condenser. After 3 h the mixture was cooled and concentrated in vacuo to give a crude oil. Purification via flash chromatography (95:5 CH$_2$Cl$_2$/MeOH) afforded 17 (0.246 g, 77%) as a pink solid; Mass Spec M+H=352. The above procedure may be used with various different phenols in step 1 and/or substituted guanidines in step 7 under essentially the same reaction conditions to produce additional compounds. Additional compounds made according to the procedure of Example 1 are shown in Table 1.

Example 2

5-(2-Isopropyl-5-methanesulfonyl-4-methoxy-phenoxy)-pyrimidine-2,4-diamine

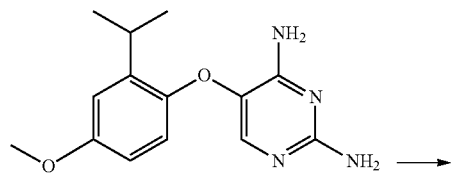

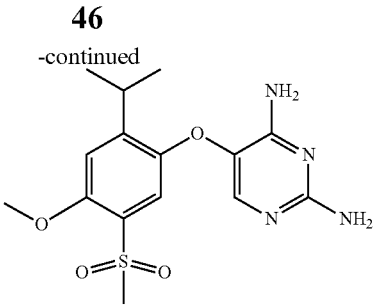

To a mixture of 5-(2-isopropyl-4-methoxy-phenoxy)-pyrimidine-2,4-diamine (0.32 g, 1.17 mmol), prepared according to Example 1, and methanesulfonic anhydride (0.81 g, 4.67 mmol) was added trifluoromethanesulfonic acid (0.45 g, 3.00 mmol), and the mixture was heated at 80° C. for 16 hrs. The reaction mixture was poured into ice water, basified with saturated NaHCO$_3$ solution and extracted into dichloromethane, which was dried over Na$_2$SO$_4$, filtered and concentrated in vacuo. The residue was purified via flash chromatography on silica gel (3% CH$_3$OH in CH$_2$Cl$_2$ with 0.1% NH$_4$OH) gave 5-(2-isopropyl-5-methanesulfonyl-4-methoxy-phenoxy)-pyrimidine-2,4-diamine as a white solid (0.248 g, 90%; 0.107 g), MS (M+H): 353.

Example 3

5-(5-Iodo-2-isopropyl-4-methoxy-phenoxy)-pyrimidine-2,4-diamine

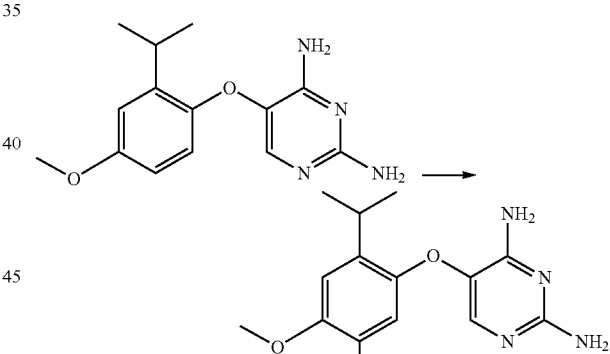

To a solution of 5-(2-isopropyl-4-methoxy-phenoxy)-pyrimidine-2,4-diamine (0.40 g, 1.44 mmol) in glacial acetic acid (4 ml) at room temperature was added a solution of iodine monochloride (0.28 g, 1.76 mmol) in glacial acetic acid (4 ml). Water (6 ml) was also added, and the reaction was stirred for 16 hours, after which another portion of iodine monochloride (0.4 g, 2.47 mmol) in glacial acetic acid (4 ml) was added. The reaction mixture was stirred for an additional hour at room temperature. The acidic mixture was basified with saturated NaHCO$_3$ solution and extracted into dichloromethane. The organic layer was dried over Na$_2$SO$_4$, filtered and concentrated in vacuo. The residue was purified via flash chromatography (5% CH$_3$OH in CH$_2$CL$_2$ with 0.1% NH$_4$OH) to give 5-(5-iodo-2-isopropyl-4-methoxy-phenoxy)-pyrimidine-2,4-diamine as beige colored solid (0.536 g, 92%). M+H 400.

Example 4

5-(2,4-Diamino-pyrimidin-5-yloxy)-4-isopropyl-2-methoxy-benzonitrile

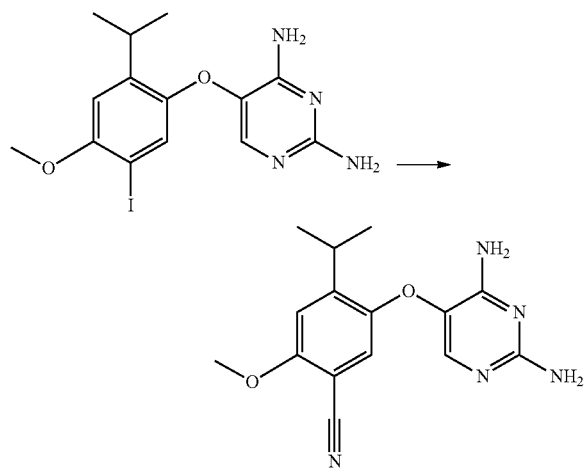

A mixture of 5-(5-iodo-2-isopropyl-4-methoxy-phenoxy)-pyrimidine-2,4-diamine (0.37 g, 0.925 mmol) and CuCN (0.12 g, 1.39 mmol) in DMF (5 ml) was heated at 120° C. for 3 hours. Water (100 ml) was added, and the precipitate was collected. The residue was triturated with methanolic dichloromethane (10% CH$_3$OH in CH$_2$Cl$_2$ with 0.1% NH$_4$OH) to release the product from its copper complex and filtered. The filtrate was concentrated and purified via flash chromatography (3% CH$_3$OH in CH$_2$Cl$_2$ with 0.1% NH$_4$OH) to give 5-(2,4-diamino-pyrimidin-5-yloxy)-4-isopropyl-2-methoxy-benzonitrile as white solid (0.12 g, 44%): M+H 300.

Example 5

1-[5-(2,4-Diamino-pyrimidin-5-yloxy)-4-isopropyl-2-methoxy-phenyl]-ethanone and 1-[5-(2,4-Diamino-pyrimidin-5-yloxy)-2-hydroxy-4-isopropyl-phenyl]-ethanone

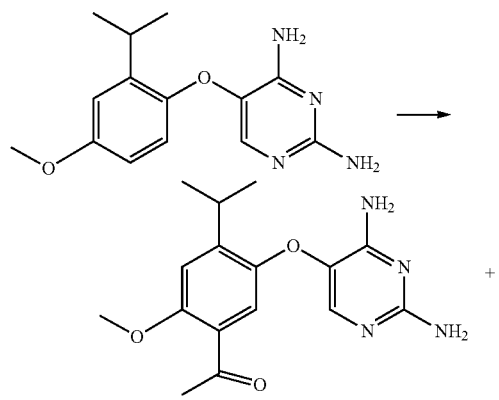

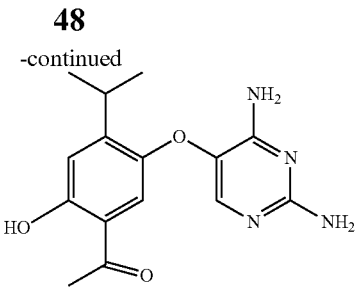

5-(2-isopropyl-4-methoxy-phenoxy)-pyrimidine-2,4-diamine in anhydrous dichloroethane (20 mL) was added to trifluoroacetic acid (0.06 mL, 0.77 mmol), acetyl chloride (0.31 mL, 4.37 mmol), and aluminum trichloride (583 mg, 4.37 mmol). After stirring for 22 hours at room temperature, water (1.2 mL) was added to the reaction at 0° C. The mixture was dried using anhydrous sodium sulfate and concentrated in vacuo. Aqueous sodium hydroxide (0.2M, 10 mL) was added to the residue and the mixture was heated at 100° C. for 1 hour. After cooling, the reaction was extracted with dichloromethane. The dichloromethane layer was dried using anhydrous magnesium sulfate, concentrated, and purified with silica gel column chromatography eluting with 96/4/0.1 dichloromethane/methanol/ammonium hydroxide to yield 1-[5-(2,4-diamino-pyrimidin-5-yloxy)-4-isopropyl-2-methoxy-phenyl]-ethanone (72 mg, 31%) as off-white solid, MS (M+H)=317. Also recovered was 1-[5-(2,4-diamino-pyrimidin-5-yloxy)-2-hydroxy-4-isopropyl-phenyl]-ethanone (43 mg, 20%) as pale yellow solid, MS (M+H)=303.

Example 6

5-(2,4-Diamino-pyrimidin-5-yloxy)-4-isopropyl-2-methoxy-benzoic acid

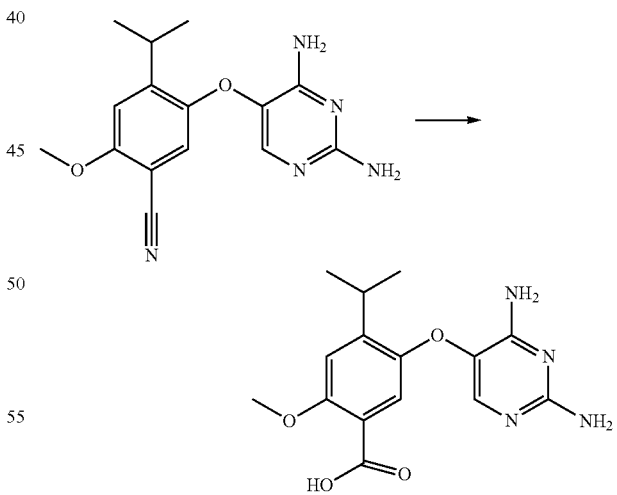

To a suspension of 5-(2,4-diamino-pyrimidin-5-yloxy)-4-isopropyl-2-methoxy-benzonitrile (50 mg, 0.17 mmol, from Example 14) in ethanol (1 mL) was added sodium hydroxide (174 mg, 4.34 mmol, dissolved in 1 mL water). After refluxing overnight, the reaction was cooled in an ice bath. Aqueous hydrochloric acid (3M) was added until the pH of the reaction was 7. The white solid precipitate was collected, washed with small amounts of water and dichloromethane, and dried to yield 5-(2,4-diamino-pyrimidin-5-yloxy)-4-isopropyl-2-methoxy-benzoic acid: (51 mg, 96%, MS (M+H)=319), which was converted to the hydrochloride salt.

Example 7

5-(2,4-Diamino-pyrimidin-5-yloxy)-4-isopropyl-2-methoxy-benzamide

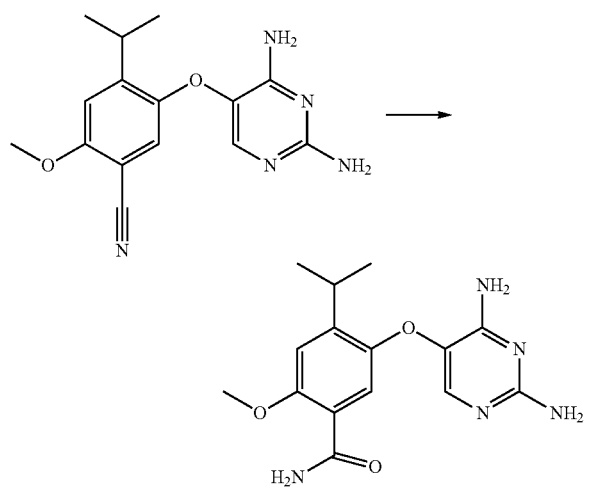

To 5-(2,4-diamino-pyrimidin-5-yloxy)-4-isopropyl-2-methoxy-benzonitrile (49 mg, 0.16 mmol, from Example 14) suspended in ethanol (1 mL) was added sodium hydroxide (64 mg, 1.60 mmol, dissolved in 1 mL water). The reaction was heated at 110° C. for 5 hours, cooled, and washed with dichloromethane (25 mL). The dichloromethane layer was concentrated and purified by preparatory TLC plates (92/8/0.5 dichloromethane/methanol/ammonium hydroxide) to yield 5-(2,4-diamino-pyrimidin-5-yloxy)-4-isopropyl-2-methoxy-benzamide as white solid (9 mg, 17%, MS (M+H)=318), which was converted to the hydrochloride salt.

Example 8

5-(2-Isopropyl-4-methoxy-5-nitro-phenoxy)-pyrimidine-2,4-diamine

The synthetic procedure used in this Example is outlined in Scheme C

SCHEME C

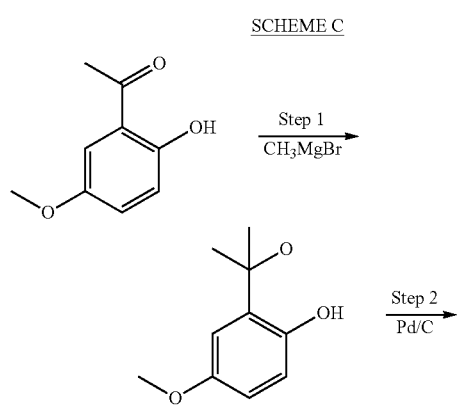

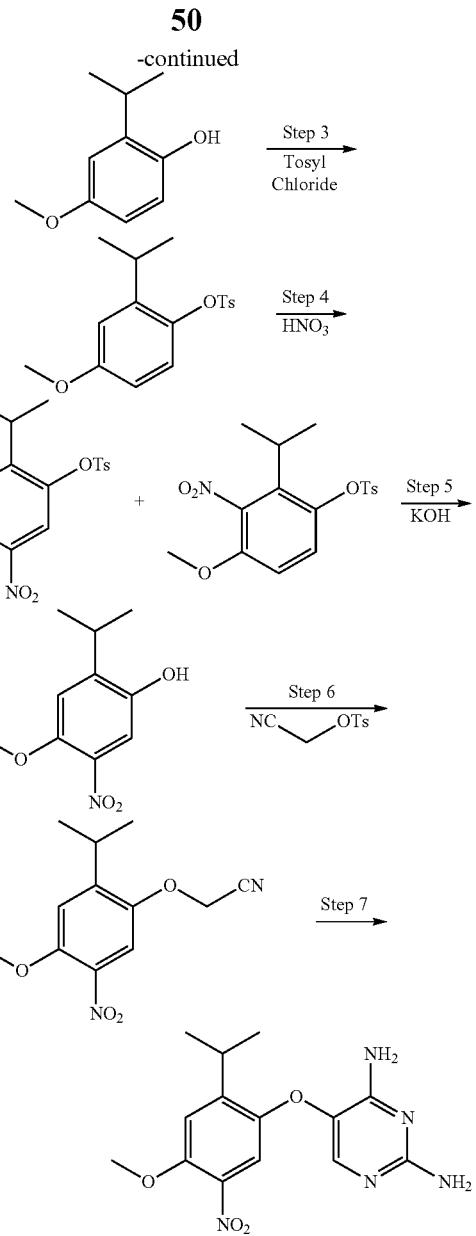

Step 1.
2-(1-Hydroxy-1-methyl-ethyl)-4-methoxy-phenol

To a solution of methylmagnesium bromide (221 ml, 665 mmol) in 800 ml THF at 0° C. was added 1-(2-hydroxy-5-methoxy-phenyl)-ethanone (20.21 g, 302 mmol) in portions over 30 min. The mixture was allowed to warm to room temperature. After 16 h the mixture was quenched by the slow addition of 10% NH$_4$Cl, carefully acidified to pH=1 (slow addition) with concentrated HCl and extracted with Et$_2$O. The combined organics were washed with H$_2$O, washed with brine, died over MgSO$_4$, filtered and concentrated in vacuo to give 2-(1-hydroxy-1-methyl-ethyl)-4-methoxy-phenol (50.57 g, 100%) as a tan solid.

Step 2. 2-Isopropyl-4-methoxy-phenol

To a solution of 2-(1-hydroxy-1-methyl-ethyl)-4-methoxy-phenol (50.57 g, 278 mmol) in 550 ml AcOH was added 10% Pd/C (as a slurry in 20 ml H₂O). Ammonium formate (87.52 g, 1388 mmol) was added in portions. The mixture was warmed to 100° C. for 1 hour, cooled and filtered through a pad of celite. The celite pad was washed with ethyl acetate. The mother liquor was mixed with H$_2$O and extracted with ethyl acetate. The combined organics were washed with H$_2$O, washed with brine, dried over Na$_2$SO$_4$, filtered and concentrated in vacuo to give 2-isopropyl-4-methoxy-phenol (44.74 g, 97%) as a pale yellow oil.

Step 3. Toluene-4-sulfonic acid 2-isopropyl-4-methoxy-phenyl ester

A solution of 2-isopropyl-4-methoxy-phenol (56.91 g, 342 mmol) triethylamine (57.3.0 ml, 411 mmol) in 750 ml CH$_2$Cl$_2$ was cooled to 0° C. p-Toluenesulfonyl chloride (68.54 g, 360 mmol) in 250 ml CH$_2$Cl$_2$ was added drop-wise at a rate that maintained the internal temperature <10 OC. The mixture was allowed to warm to rt. After 16 h, H$_2$O was added and the mixture was extracted with CH$_2$Cl$_2$. The combined organics were washed with brine, dried with Na$_2$SO$_4$, filtered and concentrated in vacuo to afford a crude solid. Recrystallization from hexanes afforded toluene-4-sulfonic acid 2-isopropyl-4-methoxy-phenyl ester (81.67 g, 74%) as white needles.

Step 4. Toluene-4-sulfonic acid 2-isopropyl-4-methoxy-5-nitro-phenyl ester

To a solution of toluene-4-sulfonic acid 2-isopropyl-4-methoxy-phenyl ester (19.00 g, 59 mmol) in 118 mL AcOH was added 236 ml fuming HNO$_3$ over 20 min. After 16 h the solution was pouring into a rapidly stirring slurry of 2 l of ice/H$_2$O. After 15 min the precipitate was filtered, washed with H$_2$O and dried under vacuum (50° C.) to give toluene-4-sulfonic acid 2-isopropyl-4-methoxy-5-nitro-phenyl ester (21.27 g, 98%) and toluene-4-sulfonic acid 2-isopropyl-4-methoxy-3-nitro-phenyl ester and as a pale yellow solid (7:1 inseparable mixture).

Step 5. 2-Isopropyl-4-methoxy-5-nitro-phenol

A solution of toluene-4-sulfonic acid 2-isopropyl-4-methoxy-5-nitro-phenyl ester and 2-isopropyl-4-methoxy-3-nitro-phenyl ester (21.20 g, 58 mmol) and 175 mL 2M KOH in 350 mL EtOH was warmed to 100° C. After 45 minutes the mixture was cooled, evaporated and taken up in 1 l of water. The solution was acidified to pH=1 with 12 M HCl and extracted with ethyl acetate. The combined organics were washed with H$_2$O, brine, dried over Na$_2$SO$_4$, filtered and concentrated in vacuo. The crude oil was purified via flash chromatography (gradient: 95:5 to 4:1 hexane/ethyl acetate) to afford 3-amino-2-isopropyl-5-nitro-phenol (10.03 g, 81%) as a yellow solid and 3-amino-2-isopropyl-3-nitro-phenol (1.32 g, 11%) as a yellow oil.

Step 6. (2-Isopropyl-4-methoxy-5-nitro-phenoxy)-acetonitrile

A mixture of 3-amino-2-isopropyl-5-nitrophenol (9.94 g, 47 mmol), K$_2$CO$_3$ (13.00 g, 94 mmol) and toluenesulfonic acid cyanomethyl ester (10.93 g, 52 mmol) in 500 mL DMF was warmed to 50° C. After 16 h the mixture was cooled, poured into 500 mL H$_2$O and extracted with toluene/ethyl acetate (1:1). The combined organics were washed with H$_2$O, washed with brine, filtered and concentrated in vacuo.

The crude solid was recrystallized from EtOH to afford (2-isopropyl-4-methoxy-5-nitro-phenoxy)-acetonitrile (8.95 g, 76%) as a yellow crystalline solid.

Step 7. 5-(2-Isopropyl-4-methoxy-5-nitro-phenoxy)-pyrimidine-2,4-diamine

A mixture of (2-isopropyl-4-methoxy-5-nitro-phenoxy)-acetonitrile (8.785 g, 35.5 mmol) and Bredereck's reagent (14.6 mL, 70.9 mmol) was warmed to 100° C. After 45 min the mixture was evaporated under reduced pressure (50° C., 50 mtorr) to give an orange solid. The solid was added to a solution of aniline hydrochloride (9.19 g, 70.9 mmol) in 150 mL of EtOH. The mixture was warmed to reflux. After 16 hr additional aniline hydrochloride (4.596 g, 35.5 mmol) was added mixture was continued at reflux for 4 h. The solution was concentrated in vacuo and poured into H$_2$O. The mixture was extracted with ethyl acetate, washed with H$_2$O, washed with brine, dried over Na$_2$SO$_4$, and concentrated in vacuo to afford a yellow-green solid. This crude product was added to a mixture of 200 mL NMP and guanidine carbonate (17.70 g, 98 mmol) and warmed to 130° C. After 5 hours the mixture was cooled then poured onto 2 l of an ice/H$_2$O mixture. The resulting precipitate was filtered, washed with H$_2$O and dried under vacuum (50° C.). The crude solid was recrystallized from EtOH to afford 5-(2-isopropyl-4-methoxy-5-nitro-phenoxy)-pyrimidine-2,4-diamine (8.14 g, 63%, 3 steps) as a yellow crystalline solid (solvated 1:1 with EtOH). (M+H)$^+$=320.

Example 9

[5-(2,4-Diamino-pyrimidin-5-yloxy)-4-isopropyl-2-methoxy-phenyl]-urea

Step 1. 5-(5-Amino-2-isopropyl-4-methoxy-phenoxy)-pyrimidine-2,4-diamine

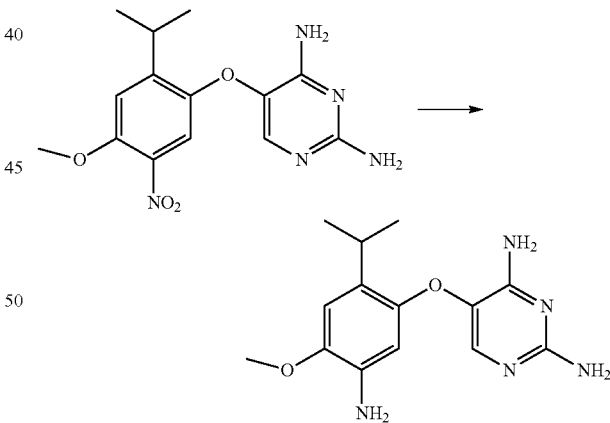

To 5-(2-isopropyl-4-methoxy-5-nitro-phenoxy)-pyrimidine-2,4-diamine (2.1 g, 6.58 mmol) suspended in ethanol (150 mL) in a Parr bomb, was added 10% palladium on charcoal (210 mg). After hydrogenation in the Parr hydrogenator overnight at 35 psi, the reaction was filtered through celite. The celite pad was washed with ethanol and ethyl acetate and the filtrate was concentrated. Purification with silica gel column chromatography (92/8/0.1 dichloromethane/methanol/ammonium hydroxide) gave 5-(5-amino-2-isopropyl-4-methoxy-phenoxy)-pyrimidine-2,4-diamine as a pale orange solid (468 mg, 25%, (M+H)$^+$=290), which was converted to the hydrochloride salt.

Step 2. [5-(2,4-Diamino-pyrimidin-5-yloxy)-4-isopropyl-2-methoxy-phenyl]-urea

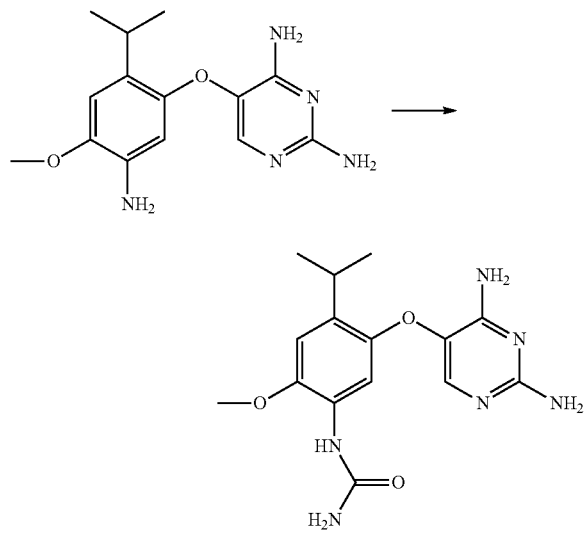

To 5-(5-amino-2-isopropyl-4-methoxy-phenoxy)-pyrimidine-2,4-diamine (314 mg, 1.09 mmol) suspended in water (3 mL) was added acetic acid (0.25 mL, 4.34 mmol). Once all solids had dissolved, sodium cyanate (71 mg, 1.09 mmol, dissolved in 1.5 mL water) was added dropwise. After 30 minutes, the reaction was concentrated and purified with silica gel column chromatography eluting with 92/8/0.1 dichloromethane/methanol/ammonium hydroxide to yield [5-(2,4-diamino-pyrimidin-5-yloxy)-4-isopropyl-2-methoxy-phenyl]-urea as an off-white solid (244 mg, 68%, M+H)$^+$=333), which was converted to a hydrochloride salt:

Example 10

N-[5-(2,4-Diamino-pyrimidin-5-yloxy)-4-isopropyl-2-methoxy-phenyl]-acetamide

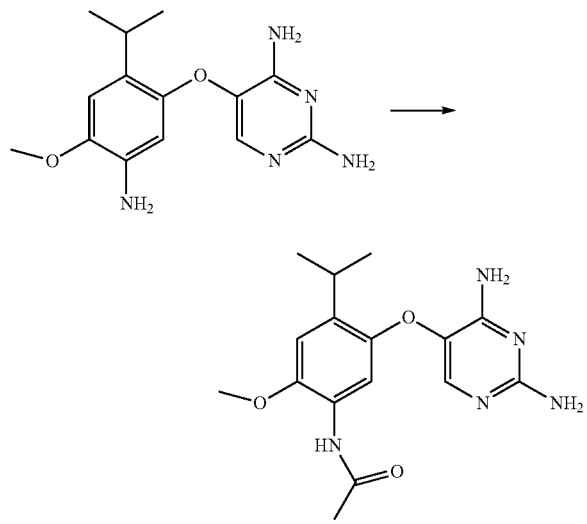

To 5-(5-amino-2-isopropyl-4-methoxy-phenoxy)-pyrimidine-2,4-diamine (100 mg, 0.35 mmol, from Example 17) dissolved in anhydrous dichloromethane (10 mL) was added anhydrous pyridine (0.03 mL, 0.38 mmol). To this reaction mixture at 0° C. was added acetyl chloride (0.03 mL, 0.38 mmol). After stirring at room temperature for 1 hour, the reaction was concentrated and purified with preparatory TLC (93/7/0.5 dichloromethane/methanol/ammonium hydroxide) to yield an off-white solid (74 mg mixture of bis- and tris-acetylated products). To this solid was added aqueous sodium hydroxide (0.2 M, 2 mL), and the mixture was refluxed for 1 hour, cooled, and washed with dichloromethane (10 mL). The dichloromethane layer was dried using anhydrous magnesium sulfate and concentrated in vacuo to yield N-[5-(2,4-diamino-pyrimidin-5-yloxy)-4-isopropyl-2-methoxy-phenyl]-acetamide as a white solid (53 mg, 46%, M+H)$^+$=332) which was converted to a hydrochloride salt:

Example 11

1-[5-(2,4-Diamino-pyrimidin-5-yloxy)-4-isopropyl-2-methoxy-phenyl]-3-ethyl-urea

Step 1. 5-(5-Amino-2-Isopropyl-4-methoxy-phenoxy)-pyrimidine-2,4-diamine

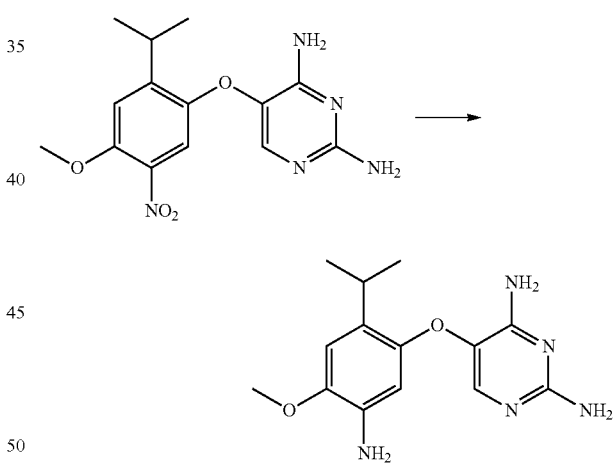

To a solution of 5-(2-isopropyl-4-methoxy-5-nitro-phenoxy)-pyrimidine-2,4-diamine (2.953 g, 9.2 mmol) in 250 mL EtOH and 25 AcOH was added 10% Pd/C. The mixture was placed under 50 psi of $H_2$ via a Parr hydrogenator. After 2.5 h the mixture was filtered through a pad of celite. The pad was washed with ethyl acetate and the solution was partially concentrated in vacuo. The residue was taken up in 500 mL $H_2O$ and cooled to 0° C. The solution was adjusted to pH=12 with 50% NaOH extracted with ethyl acetate. The combined organics were washed with $H_2O$, washed with brine, dried over $Na_2SO_4$, filtered and concentrated in vacuo to afford 5-(5-amino-2-Isopropyl-4-methoxy-phenoxy)-pyrimidine-2,4-diamine (2.156 g, 82%) as a dark-orange solid.

Step 2. 1-[5-(2,4-Diamino-pyrimidin-5-yloxy)-4-isopropyl-2-methoxy-phenyl]-3-ethyl-urea

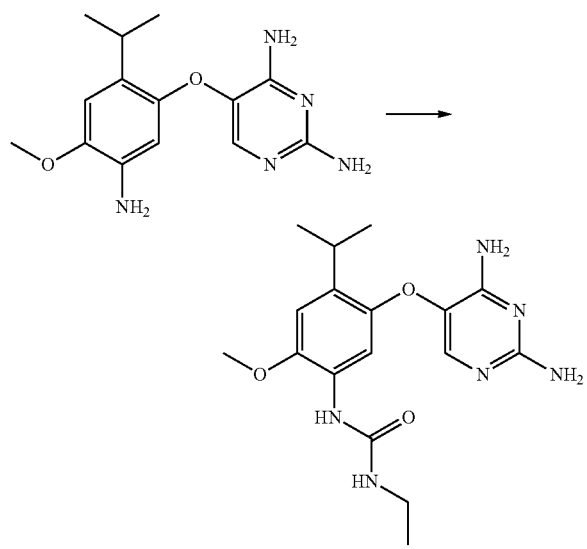

A solution of 5-(5-amino-2-Isopropyl-4-methoxy-phenoxy)-pyrimidine-2,4-diamine (0.117 g, 0.4 mmol) and ethyl isocyanate (0.034 g, 0.5 mmol) in 4 mL of toluene was heated to 100° C. in a sealed tube. After 5 h the solution was cooled and concentrated in vacuo gave a brown solid. Purification via flash chromatography (CH$_2$Cl$_2$/MeOH 97:3) afforded 1-[5-(2,4-diamino-pyrimidin-5-yloxy)-4-isopropyl-2-methoxy-phenyl]-3-ethyl-urea (0.120 g, 83%) as a white solid; (M+H)=361.

Example 12

1-[5-(2,4-diamino-pyrimidin-5-yloxy)-4-isopropyl-2-methoxy-phenyl]-3-phenyl-urea

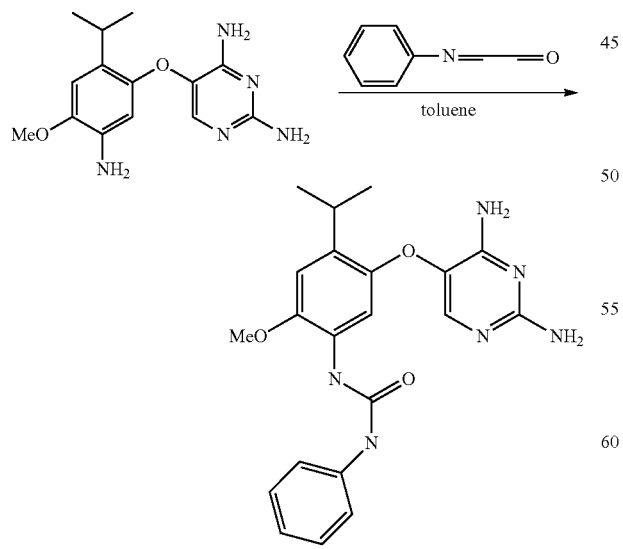

5-(5-amino-2-Isopropyl-4-methoxy-phenoxy)-pyrimidine-2,4-diamine (0.309 g, 1.1 mmol) was converted, as described in the above procedure, to 1-[5-(2,4-diamino-pyrimidin-5-yloxy)-4-isopropyl-2-methoxy-phenyl]-3-phenyl-urea (0.122 g, 28%) as white solid; [MH]$^+$=408.

Similarly prepared from 5-(5-amino-2-Isopropyl-4-methoxy-phenoxy)-pyrimidine-2,4-diamine (0.313 g, 1.1 mmol) and 2,5-hexanedione (0.14 ml, 1.2 mmol) was 5-[5-(2,5-Dimethyl-pyrrol-1-yl)-2-isopropyl-4-methoxy-phenoxy]-pyrimidine-2,4-diamine, (0.259 g, 64%). (M+H)=368.

Example 13

4-Chloro-N-[5-(2,4-diamino-pyrimidin-5-yloxy)-4-isopropyl-2-methoxy-phenyl]-butyramide

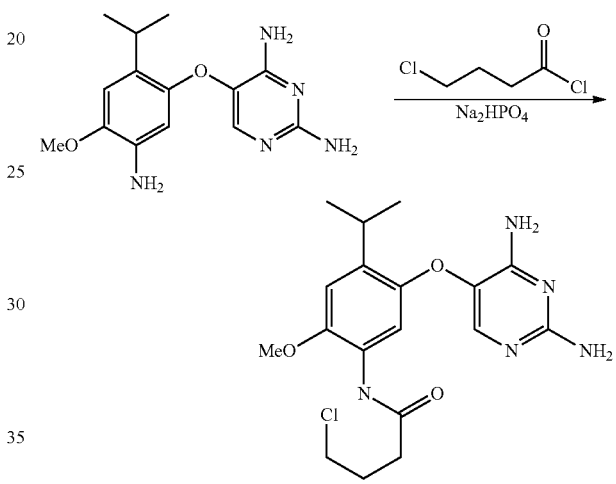

To a solution of 5-(5-amino-2-isopropyl-4-methoxy-phenoxy)-pyrimidine-2,4-diamine (0.400 g, 1.4 mmol) in 15 ml CHCl$_3$ and Na$_2$HPO$_4$ (0.392 g, 2.8 mmol) was added 4-chlorobutyryl chloride (0.194 g, 1.4 mmol) drop-wise. After 4.5 h, H$_2$O and CH$_2$Cl$_2$ were added and the mixture was allowed to stir 15 min. The mixture was neutralized with 2N Na$_2$CO$_3$ and extracted with CH$_2$Cl$_2$. The combined organics were washed with brine, dried over Na$_2$SO$_4$, filtered and concentrated in vacuo to afford 4-chloro-N-[5-(2,4-diamino-pyrimidin-5-yloxy)-4-isopropyl-2-methoxy-phenyl]-butyramide (0.495 g, 91%) as brown foam; [MH]$^+$=394.

Example 14

5-(2-Isopropyl-5-isothiocyanato-4-methoxy-phenoxy)-pyrimidine-2,4-diamine

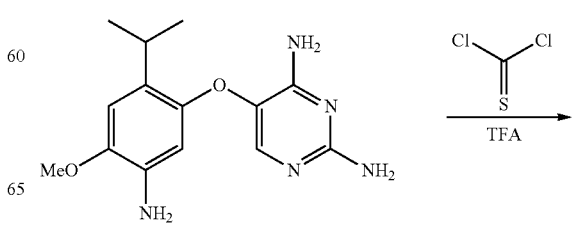

-continued

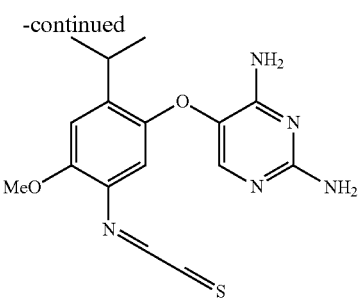

To a solution of 5-(5-amino-2-isopropyl-4-methoxy-phenoxy)-pyrimidine-2,4-diamine (0.100 g, 0.4 mmol) in 1 ml H₂O and TFA (0.040 g, 0.4 mmol) was added thiophosgene (0.040 g, 0.4 mmol). After 1 h the mixture was neutralized with 2M NaOH and extracted with CH₂Cl₂. The combined organics were washed with brine, dried over Na₂SO₄, filtered and concentrated in vacuo to afford 5-(2-isopropyl-5-isothiocyanato-4-methoxy-phenoxy)-pyrimidine-2,4-diamine (0.042 g, 36%) as brown foam [MH]⁺=334.

Example 15

2-[5-(2,4-Diaminopyrimidin-5-yloxy)-4-isopropyl-2methoxy-phenyl]-propan-2-ol

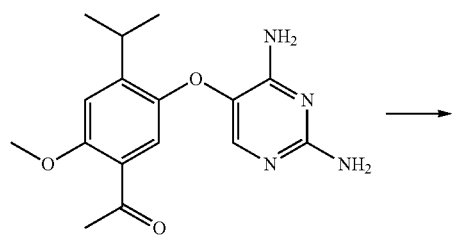

To a solution of methylmagnesium bromide (83.4 mmol, 27.8 ml, 3.0 M in Et₂O) in 83 mL THF at 0° C. was added 1-[5-(2,4-diamino-pyrimidin-5-yloxy)-4-isopropyl-2-methoxy-phenyl]-ethanone (2.523 g, 8.3 mmol, from Example 16) in portions. After 16 h the mixture was cooled to 0° C. and was quenched by the addition 10% NH₄Cl. H₂O was added and the mixture was extracted with ethyl acetate. The combined organics were washed with H₂O, washed with brine, dried over NaHCO₃, filtered and concentrated in vacuo. The crude solid was taken up in 31 ml DMF. K₂CO₃ (0.65 g, 4.7 mmol) and iodomethane (0.098 ml, 1.6 mmol) were added and the mixture was warmed to 50° C. Additional portions of iodomethane (0.019 mL, 0.6 mmol) was added at 1, 2 and 3 hr. After 16 h the mixture was cooled and 10% NH₄Cl and extracted with ethyl acetate. The combined organics were washed with H₂O, washed with brine, dried with Na₂SO₄, filtered and concentrated in vacuo to give 2-[5-(2,4-diaminopyrimidin-5-yloxy)-4-isopropyl-2-methoxy-phenyl]-propan-2-ol (0.711 g, yield) as a white solid. [MH]⁺=333.

Example 16

5-(2,5-Diisopropyl-methoxy-phenoxy)-pyrimidine-2,4-diamine

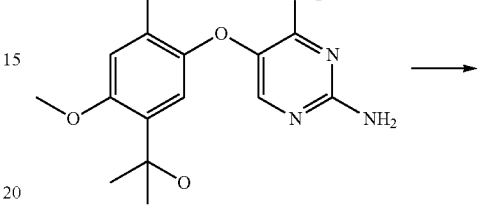

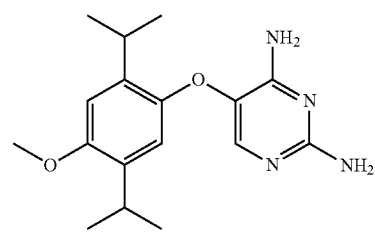

To a solution of 2-[5-(2,4-diaminopyrimidin-5-yloxy)-4-isopropyl-2-methoxy-phenyl]-propan-2-ol: (0.350 g, 1.1 mmol) in 10 ml CH₂Cl₂ was added trifluoroacetic acid (4.0 ml, 52.6 mmol) and triethylsilane (1.7 ml, 10.5 mmol). After 30 min saturated NaHCO₃ was added and the mixture was extracted with ethyl acetate. The combined organics were washed with brine, dried over Na₂SO₄, filtered and concentrated in vacuo to give a crude oil. Purification via flash chromatography (96:4 CH₂Cl₂/MeOH) gave 5-(2,5-diisopropyl-methoxy-phenoxy)-pyrimidine-2,4-diamine (0.225 g, 68%) as a white solid. [MH]⁺=317.

Example 17

1-[5-(2,4-Diamino-pyrimidine-5-yloxy)-4-isopropyl-2-methoxy-phenyl]-ethanol

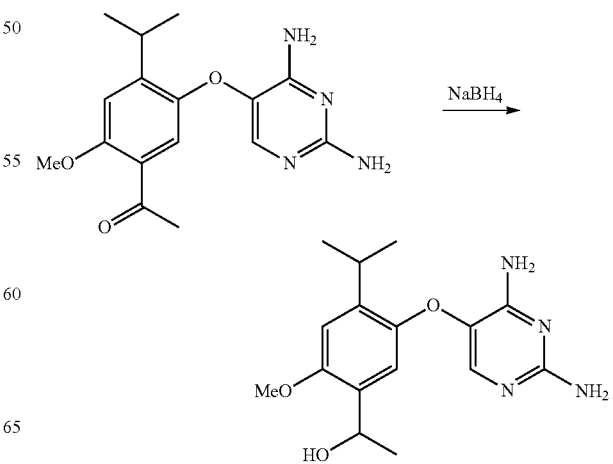

To a solution of 1-[5-(2,4-diamino-pyrimidin-5-yloxy)-4-isopropyl-2-methoxy-phenyl]-ethanone (2.500 g, 8.3 mmol) in 100 ml MeOH was slowly added NaBH$_4$ (1.566 g, 41.4 mmol) at 0° C. The solution was allowed to warm to rt. After 20 h, the saturated NH$_4$Cl was added, the mixture was concentrated in vacuo and extracted with ethyl acetate. The combined organics were washed with brine, dried over Na$_2$SO$_4$, filtered and concentrated in vacuo. Purification via silica gel column chromatography (9:1 CH$_2$Cl$_2$/MeOH) afforded to 1-[5-(2,4-diamino-pyrimidine-5-yloxy)-4-isopropyl-2-methoxy-phenyl]-ethanol (1.613 g, 60%) as white foam; [MH]$^+$=301.

Example 18

5-(2-Isopropyl-4-methoxy-5-vinyl-phenoxy)-pyrimidine-2,4-diamine and 5-[2-Isopropyl-4-methoxy-5-(1-methoxy-ethyl)-phenoxy]-pyrimidine-2,4-diamine

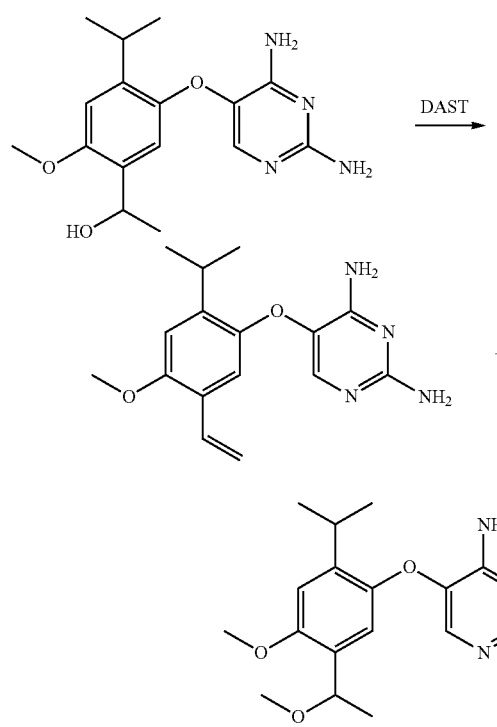

To a solution of 1-[5-(2,4-Diamino-pyrimidin-5-yloxy)-4-isopropyl-2-methoxy-phenyl]-ethanol (1.613 g, 5.3 mmol) in 30 ml CH$_2$Cl$_2$ at −78 OC was added DAST (0.935 g, 5.8 mmol). After stirring 1.5 h, saturated NaHCO$_3$ was added and the mixture was extracted by CH$_2$Cl$_2$. The combined organics were washed with brine and dried Na$_2$SO$_4$, filtered and concentrated in vacuo. Purification via silica gel chromatography (95:5 CH$_2$Cl$_2$/MeOH) gave 5-(2-Isopropyl-4-methoxy-5-vinyl-phenoxy)-pyrimidine-2,4-diamine (0.044 g, 3%) as a foam ([MH]$^+$=301) and 5-[2-Isopropyl-4-methoxy-5-(1-methoxy-ethyl)-phenoxy]-pyrimidine-2,4-diamine (0.075 g, 4%) as foam. [MH]$^+$=303.

Example 20

5-(2,4-Diamino-pyrimidin-5-yloxy)-4-isopropyl-2-methoxy-N-methyl-benzenemethylsulfonamide Step 1. 5-(2,4-Diamino-pyrimidin-5-yloxy)-4-isopropyl-2-methoxy-benzenesulfonyl chloride

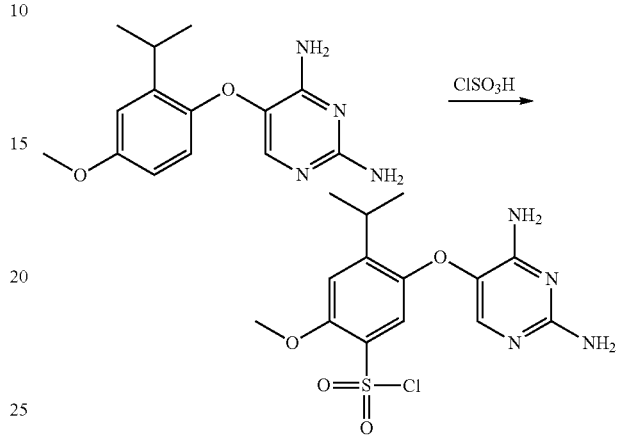

A mixture of pyrimidine (0.400 g, 1.5 mmol) in 2 ml chlorosulfonic acid was allowed to stir 20 min. The mixture was poured over ice. The precipitate was filtered, washed by cold H$_2$O and dried under vacuum to afford 5-(2,4-diamino-pyrimidin-5-yloxy)-4-isopropyl-2-methoxy-benzenesulfonyl chloride (0.515 g, 95%) as a white solid; [MH]$^+$=373.

Step 2. 5-(2,4-Diamino-pyrimidin-5-yloxy)-4-isopropyl-2-methoxy-N-methyl-benzenemethylsulfonamide

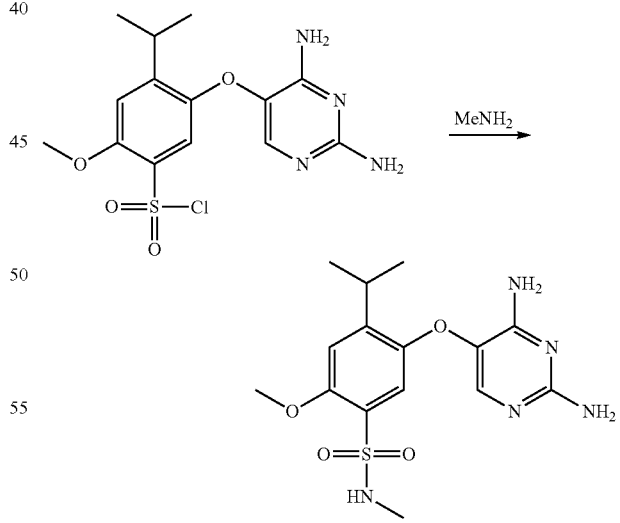

To 10 ml methyl amine −78° C. in a screw-capped tube was added 5-(2,4-diamino-pyrimidin-5-yloxy)-4-isopropyl-2-methoxy-benzenesulfonyl chloride (0.300 g, 0.8 mmol). The mixture was allowed to warm to room temperature. After 20 hours the mixture was evaporated, washed with H$_2$O, and dried under vacuum to afford 5-(2,4-diamino-pyrimidin-5-yloxy)-4-idopropyl-2-methoxy-N-methyl-benzenemethylsulfonamide (0.170 g, 57%) as a white solid; mp (HCl salt)=252.3-252.9° C.; [MH]+=367.

Similarly prepared, replacing methylamine with ethylamine, was 5-(2,4-Diamino-pyrimidin-5-yloxy)-N-ethyl-4-isopropyl-2-methoxy-benzenesulsonamide (0.186 g, 61%) as a white solid; mp (HCl salt)=260-265° C.; [MH]+=382.

Example 21

5-(2,4-Diamino-pyrimidin-5-yloxy)4-isopropyl-2-methoxy-N,N-dimethyl-benzamide

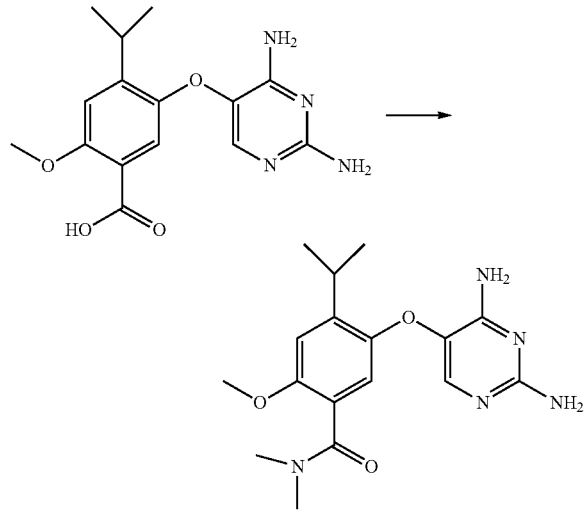

To a suspension of 5-(2,4-Diamino-pyrimidin-5-yloxy)-4-isopropyl-2-methoxy-benzoic acid (180 mg, 0.57 mmol, from Example 17) in anhydrous dichloromethane (5.6 mL) was added trifluoroacetic acid (0.08 mL, 1.14 mmol) and then thionyl chloride (0.36 mL, 5.65 mmol). After 1 hour the reaction was concentrated. To the residue was added anhydrous dichloromethane (4.5 mL) and dimethylamine (2.84 mL of a 2M solution in tetrahydrofuran, 5.65 mmol). After 2 hours stirring at room temperature, the reaction was filtered and concentrated. Purification via silica gel column chromatography eluting with 95/5/0.1 to 93/7/0.1 dichloromethane/methanol/ammonium hydroxide yielded 5-(2,4-diamino-pyrimidin-5-yloxy)4-isopropyl-2-methoxy-N,N-dimethyl-benzamide (40 mg, 20%) as pale yellow solid, MS (M+H)=346.

Similarly prepared using methylamine instead of dimethylamine, 5-(2,4-diamino-pyrimidin-5-yloxy)-4-isopropyl-2-methoxy-N-methyl-benzamide (23 mg, 15%) was prepared as pale yellow solid, MS (M+H)=332.

Example 22

4-(2,4-Diamino-pyrimidin-5-yloxy)-2-iodo-5-isopropyl-phenol

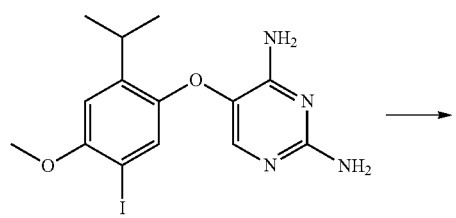

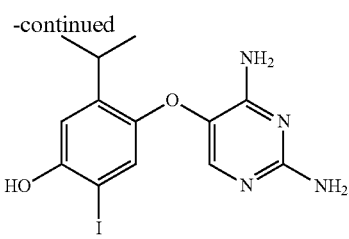

To a cold suspension of 1 (0.21 g, 0.52 mmol) in dichloromethane (15 ml) at OoC was added BBr3 (0.26 g, 1.05 mmol). The reaction mixture was stirred at room temperature for 16 hrs., quenched with water and basified with sat. NaHCO₃. The insoluble solid was collected by filtration. The filtrate was washed with water, dried over Na₂SO₄, filtered and concentrated in vacuo. The combined residue was purified via flash chromatographed on silica gel (3 to 5% methanol in dichloromethane with o.1% NH₄OH) gave desired product (0.174 g, 86%), (M+H)=387.

Example 23

5-(5-Iodo-2-isopropyl-4-prop-2-ynyloxy-phenoxy)-pyrimidine-2,4-diamine

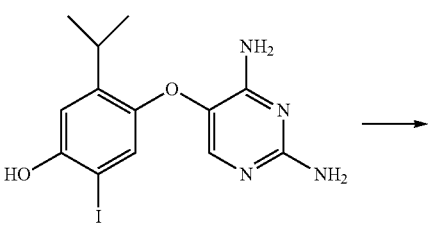

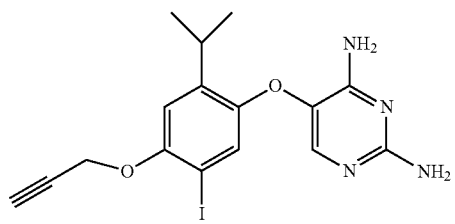

To 4-(2,4-Diamino-pyrimidin-5-yloxy)-2-iodo-5-isopropyl-phenol (200 mg, 0.43 mmol) dissolved in anhydrous N,N-dimethylformamide (2 mL) was added anhydrous potassium carbonate (414 mg, 3.00 mmol) and propargyl chloride (0.03 mL, 0.43 mmol). After stirring at room temperature overnight, the reaction was extracted with dichloromethane, water and brine. The dichloromethane layer was dried using anhydrous magnesium sulfate, concentrated, and purified via silica gel column chromatography (95/5/0.1 dichloromethane/methanol/ammonium hydroxide) to yield 5-(5-iodo-2-isopropyl-4-prop-2-ynyloxy-phenoxy)-pyrimidine-2,4-diamine as white solid (131 mg, 71%), MS (M+H) =425.

Example 24

5-(5-Ethanesulfonyl-2-isopropyl-4-methoxy-phenoxy)-pyrimidine-2,4-diamine

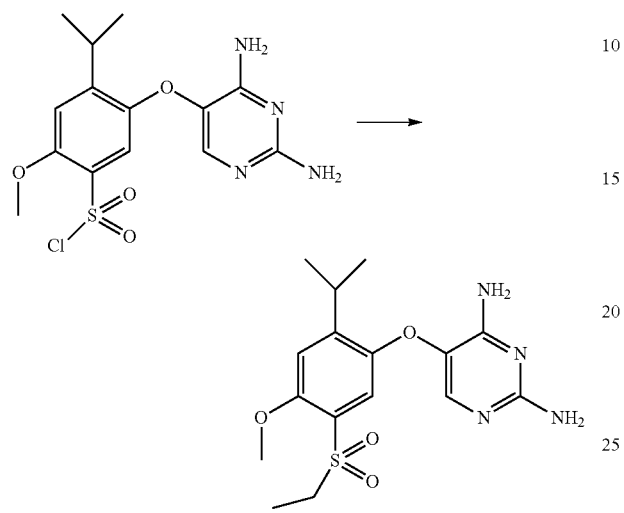

To a solution of sodium sulfite (541 mg, 4.29 mmol) in water (20 mL) was added 5-(2,4-Diamino-pyrimidin-5-yloxy)-4-isopropyl-2-methoxy-benzenesulfonyl chloride (400 mg, 1.07 mmol) and the reaction was heated at 80° C. for 1 hour. Sodium bicarbonate (361 mg, 4.29 mmol-dissolved in 5 mL water), dioxane (20 mL), and ethyl iodide (0.10 mL, 1.29 mmol) were added and the reaction was heated at 80° C. for 2 hours. The reaction was concentrated, extracted with dichloromethane (150 mL) and water (20 mL). The dichloromethane layer was dried using anhydrous sodium sulfate, concentrated, and purified via silica gel column chromatography (95/5/0.1 dichloromethane/methanol/ammonium hydroxide) to yield 5-(5-ethanesulfonyl-2-isopropyl-4-methoxy-phenoxy)-pyrimidine-2,4-diamine (77 mg, 20%) as white solid, MS (M+H)=367.

Example 25

5-(2-Isopropyl-4-methoxy-5-trifluoromethyl-phenoxy)-pyrimidine-2,4-diamine

The synthetic procedure used in this Example is outlined in Scheme E.

SCHEME E

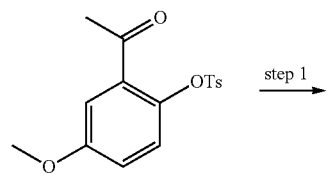

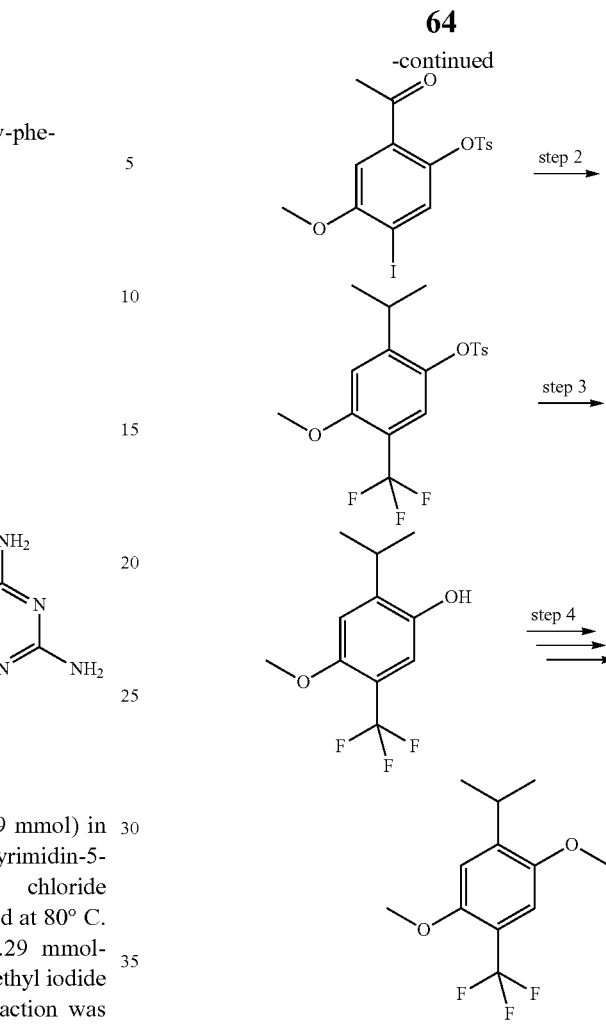

Step 1. 1-Iodo-4-isopropyl-2-methoxy-5-(toluene-4-sulfonyl)-benzene

To a solution of 2-Isopropyl-4-methoxy-1-(toluene-4-sulfonyl)-benzene (10 g, 31.25 mmol) in HOAc (10 ml) was added a solution of ICl (9.6 g, 59.26 mmol) in HOAc (10 ml) and H$_2$O (5 ml). The reaction mixture was stirred at room temperature for 16 hrs and basified by saturated NaHCO$_3$ solution. The aqueous solution was extracted into EtOAc which was washed with water, brine, dried over Na$_2$SO$_4$, filtered and concentrated in vacuo to give 1-Iodo-4-isopropyl-2-methoxy-5-(toluene-4-sulfonyl)-benzene (12.35 g, 89%).

Step 2. 1-Isopropyl-5-methoxy-2-(toluene-4-sulfonyl)-4-trifluoromethyl-benzene To a hot mixture of 1-Iodo-4-isopropyl-2-methoxy-5-(toluene-4-sulfonyl)-benzene (0.5 g, 1.12 mmol), CuI, KF in anhydrous DMF (10 ml) at 120° C. oil bath temperature, was added trifluoromethyl iodide (0.64 g, 4.48 mmol) in portions over 30 min. The reaction mixture was heated for 4 hrs and poured into H$_2$O (100 ml). The insoluble solid, which was collected by filtration was triturated with methylene chloride, filtered and concentrated to give 1-Isopropyl-5-methoxy-2-(toluene-4-sulfonyl)-4-trifluoromethyl-benzene (0.45 g, 100%) as a solid.

Step 3. 2-Isopropyl-4-methoxy-5-trifluoromethyl-phenol

A solution of 1-Isopropyl-5-methoxy-2-(toluene-4-sulfonyl)-4-trifluoromethyl-benzene (0.40 g, 1.03 mmol) and NaOH (0.5 g, 12.5 mmol) in MeOH (5 ml) and H$_2$O (5 ml) was heated at 90° C. for 2 hrs. The cooled reaction mixture was acidified with 3N HCl and extracted into methylene chloride. The combined extracts was dried with Na$_2$SO$_4$, filtered and concentrated to give desired 2-Isopropyl-4-methoxy-5-trifluoromethyl-phenol (0.194 g, 81%) as an oil.

Step 4. 5-(2-Isopropyl-4-methoxy-5-trifluoromethyl-phenoxy)-pyrimidine-2,4-diamine Following the procedure of Example 2 steps 5-7, 2-Isopropyl-4-methoxy-5-trifluoromethyl-phenol was converted to 5-(2-Isopropyl-4-methoxy-5-trifluoromethyl-phenoxy)-pyrimidine-2,4-diamine. (M+H)=343

Example 26

5-(2,4-Diamino-pyrimidin-5-yloxy)-4-isopropyl-2-methoxy-thiobenzamide

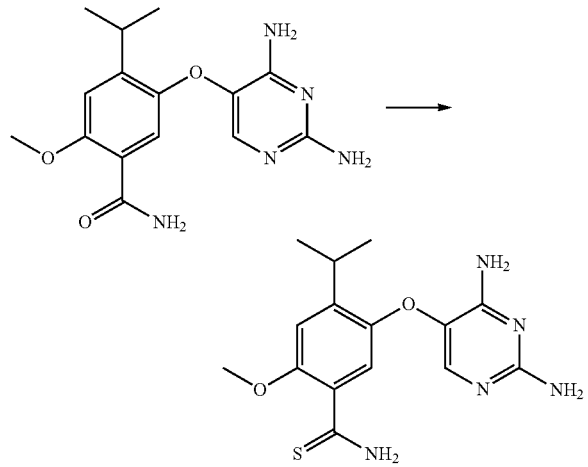

A mixture of 5-(2,4-Diamino-pyrimidin-5-yloxy)-4-isopropyl-2-methoxy-benzamide (0.25 g, 0.79 mmol, prepared according to the procedure of Example 52) and Lawesson's reagent (0.96 g, 2.37 mmol) in anhydrous THF (20 ml) was stirred at room temperature for 16 hrs and concentrated in vacuo. Flash chromatography on silica (5% CH$_3$OH in methylene chloride with 1% NH$_4$OH) gave 5-(2,4-Diamino-pyrimidin-5-yloxy)-4-isopropyl-2-methoxy-thiobenzamide (0.201 g, 76%) as a yellow solid.

Example 27

5-(4-Ethoxy-5-iodo-2-isopropyl-phenoxy)-pyrimidine-2,4-diamine

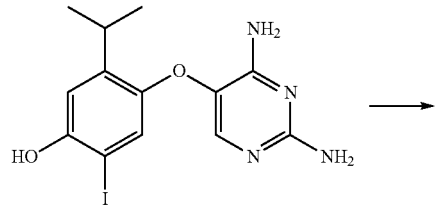

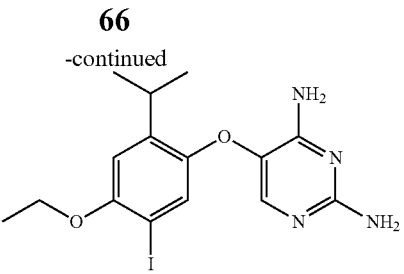

To a solution of 4-(2,4-Diamino-pyrimidin-5-yloxy)-2-iodo-5-isopropyl-phenol (0.2 g, 0.52 mmol) in anhydrous DMF (2 ml) was added EtBr (57 mg, 0.52 mmol) in portions. The reaction mixture was partitioned between EtOAc and H$_2$O. The organic extract was dried over Na$_2$SO$_4$, filtered and concentrated. Flash chromatography on silica (3% MeOH in methylene chloride with 1% NH$_4$OH) gave 5-(4-Ethoxy-5-iodo-2-isopropyl-phenoxy)-pyrimidine-2,4-diamine (0.17 g, 28%) as a yellow solid. (M+H)=415.

Example 28

Diaminopyrimidine Antagonists of P2X3 and P2X2/3 ATP-Gated Channels Produce an Effective Suppression of Systolic and Diastolic Blood Pressure in the Spontaneously Hypertensive Rats (SHRs)

The effect of aryloxydiaminopyrimidine P2X3 receptor antagonists (a compound of formula (I)) in the sensitization of these afferents in SH rats was investigated. Studies were performed to investigate the efficacy of intravenous administration of selective doses of these antagonistic compounds in SH rats as a model for human disease looking at instrumentally monitored blood pressure, sympathetic nerve discharge, and excitability of petrosal chemosensory carotid sinus afferents.

Summary of investigations and key results.

In the SH rat, denervation of the carotid bodies bilaterally produced a precipitous fall in arterial pressure (FIG. 2A); no such effect was observed in normotensive Wistar rat. Moreover, there was ~55% reduction in sympathetic discharge following denervation of the carotid bodies. These data generated the hypothesis that in addition to the heightened peripheral chemoreflex sympathoexcitatory response in SH versus Wistar rats (Tan et al. 2010, *Circulation Research* 106, 536-545), there was also aberrant discharge emanating from the carotid body of SH rats.

Intracellular recordings from petrosal ganglion chemoreceptive primary afferents confirmed the presence of aberrant chemoreceptor tonicity present in SH rats (FIG. 2B; Moraes & Paton—unpublished data). In addition, SH rat chemosensitive petrosal neurones were more depolarized and showed exaggerated responses to stimuli compared to those recorded from normotensive rats (Fig B).

Administration of P2X3 antagonist (a compound of formula (I); 1 mg·kg$^{-1}$ i.v.) reduced arterial pressure in SH rats but had no effect in Wistar normotensive rats (FIG. 2C; Pijacka & Paton—unpublished data). Importantly, the reduction in arterial pressure in SH rats was dependent on intact chemoreceptors as bilateral carotid ablation abolished the effect of the compound of formula I. These data from a relevant model for human disease support the notion that blockade of P2X3 receptors provides a novel form of anti-hypertensive therapy that acts by blocking carotid body aberrant discharge, and in turn reduces excess sympathetic discharge.

FIG. 2B shows that the aberrant discharge of chemosensitive petrosal neurons in SH rats can be completely blocked by a compound of formula (I), a P2X3 antagonist, yet these neurones maintain an ability to respond to a chemoreceptor stimulus. This is important as it effectively permits maintenance of the ability to sense hypoxia/hypercapnia and low plasma pH but prevents the aberrant discharge causing sympathoexcitation and the pathological effects this causes.

It is known that mammalian *glomus* cells release ATP when exposed to hypoxia and other chemical signals. FIG. 2D depicts the presence of P2X3 receptors in the carotid body taken from a hypertensive human subject. Note the pattern of expression is consistent with these receptors being on primary afferent terminals.

Example 29

Exemplary Tablet Formulations

A compound of formula (I) (such as a compound of Table 1) or other representative diaminopyrimidine P2X3 antagonists may be supplied formulated in a yellow, film-coated, oval-shaped tablet containing 10, 30, 50, 75, 100 or 300 mg of compound. Tablets may be formulated with USP/NF compendial grade lactose monohydrate, hydroxypropyl methyl cellulose (HPMC or Hypromellose), croscarmellose sodium, microcrystalline cellulose (Avicel PH102), and magnesium stearate as described in the Table 2 (below). Tablets are film-coated with Opadry Yellow (Colorcon, Inc.) and packaged in HDPE bottles with child resistant caps and induction seals.

TABLE 2

Compound 16 (Compound of Formula (I): Quantitative Tablet Composition (300 mg & Placebo)

| Component | Grade | Function | Amount for 300 mg Tablet (mg) | Amount for Placebo Tablet (mg) |
|---|---|---|---|---|
| Intragranular | | | | |
| Compound X (Formula (I)) (milled) | In house | Active | 300.0 | 0 |
| Lactose monohydrate | USP/NF | Diluent | 187.8 | 487.8 |
| Croscarmellose sodium | USP/NF | Disintegrant | 18.0 | 18.0 |
| Hydroxypropyl methyl cellulose | USP/NF | Binder | 18.0 | 18.0 |
| Extragranular | | | | |
| Croscarmellose sodium | USP/NF | Disintegrant | 12.0 | 12.0 |
| Microcrystalline Cellulose | USP/NF | Diluent | 60.0 | 60.0 |
| Magnesium Stearate | USP/NF | Lubricant | 4.2 | 4.2 |
| Core Tablet | | | 600 | 600 |
| Film Coating | | | | |
| Opadry Yellow 03K12429 | * | Film-coat | 18.0 | 18.0 |
| Sterile Water for Irrigation | USP/NF | Granulating Solution | As needed | As needed |
| Total Weight of Film Coated Tablet | | | 618 | 618 |

* Opadry Yellow is composed of the following USP/NF excipients: hypromellose, titanium dioxide, talc, triacetin and yellow iron oxide.

Example 30

P2X3/P2X2/3 FLIPR (Fluorometric Imaging Plate Reader) Assay

CHO-K1 cells were transfected with cloned rat P2X3 or human P2X2/3 receptor subunits and passaged in flasks. 18-24 hours before the FLIPR experiment, cells were released from their flasks, centrifuged, and re-suspended in nutrient medium at $2.5 \times 10^5$ cells/ml. The cells were aliquoted into black-walled 96-well plates at a density of 50,000 cells/well and incubated overnight in 5% $CO_2$ at 37° C. On the day of the experiment, cells were washed in FLIPR buffer (calcium- and magnesium-free Hank's balanced salt solution, 10 mM HEPES, 2 mM $CaCl_2$, 2.5 mM probenecid; FB). Each well received 100 µl FB and 100 µl of the fluorescent dye Fluo-3 AM [2 µM final conc.]. After a 1 hour dye loading incubation at 37° C., the cells were washed 4 times with FB, and a final 75 µl/well FB was left in each well.

Test compounds (dissolved in DMSO at 10 mM and serially diluted with FB) or vehicle were added to each well (25 µl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 µl/well antagonist or vehicle addition. The antagonist was a 2× solution of α,β-meATP producing a final concentration of 1 µM (P2X3) or 5 µM (P2X2/3). Fluorescence was measured for an additional 2 minutes at 1 second intervals after antagonist addition. A final addition of ionomycin (5 µM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using non-linear regression. PPADS, a standard P2X antagonist, was used as a positive control.

Using the above procedure, compounds of the invention exhibited activity for the P2X3 receptor. The compound 4-(2,4-Diamino-pyrimidin-5-yloxy)-2-iodo-5-isopropyl-phenol, for example, exhibited a $pIC_{50}$ of approximately 8.3 using the above assay.

EQUIVALENTS

While the present technologies, methods, and inventions have been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method of treating sleep apnea in a subject in need thereof, comprising administering to the subject an effective amount compound of formula (I):

(Formula I)

or a pharmaceutically acceptable salt thereof, wherein:
$R^1$ is hydrogen or $C_1$-$C_6$ alkyl optionally substituted with one to three substituents independently selected from halogen, nitro, cyano, and hydroxy; and
$R^2$ is $C_1$-$C_6$ alkyl, $C_2$-$C_6$ alkenyl, $C_2$-$C_6$ alkynyl, amino, aminosulfonyl, halo, amido, $C_1$-$C_6$ haloalkyl, $C_1$-$C_6$ alkoxy, $C_1$-$C_6$ hydroxy, $C_1$-$C_6$ haloalkoxy, nitro, $C_1$-$C_6$ hydroxyalkyl, $C_1$-$C_6$ alkoxyalkyl, $C_1$-$C_6$ hydroxyalkoxy, $C_2$-$C_6$ alkynylalkoxy; $C_1$-$C_6$ alkylsulfonyl, $C_6$-$C_{10}$ arylsulfonyl, $C_1$-$C_6$ carboxyalkyl, cyano, or $C_1$-$C_6$ alkylcarbonyl.

2. The method of claim 1, wherein the sleep apnea is central sleep apnea.

3. The method of claim 1, wherein the sleep apnea is obstructive sleep apnea.

4. The method of claim 1, wherein the sleep apnea is mixed sleep apnea.

5. The method of claim 1, wherein the sleep apnea occurs more than about 5 apneic events per hour of sleep.

6. The method of claim 1, wherein the sleep apnea occurs more than about 15 apneic events per hour of sleep.

7. The method of claim 1, wherein the sleep apnea occurs more than about 25 apneic events per hour of sleep.

8. The method of claim 1, wherein the compound of formula (I) is:

or a pharmaceutically acceptable salt thereof.

9. The method of claim 1, wherein the compound of formula (I) is a pharmaceutically acceptable salt of:

10. The method of claim 1, wherein the compound of formula (I) is:

or a pharmaceutically acceptable salt.

11. The method of claim 1, comprising administering to the subject an effective amount of a compound of formula (I) wherein $R^1$ is $C_1$-$C_6$ alkyl optionally substituted with one to three halogens, or a pharmaceutically acceptable salt thereof.

12. The method of claim 1, comprising administering to the subject an effective amount of a compound of formula (I) wherein $R^1$ is $C_1$-$C^6$ alkyl, or a pharmaceutically acceptable salt thereof.

13. A method of treating sleep apnea in a subject in need thereof, comprising administering to the subject an effective amount of the following compound:

or a pharmaceutically acceptable salt thereof.

14. The method of claim 13, comprising administering to the subject an effective amount of the following compound:

15. The method of claim 13, wherein the sleep apnea is central sleep apnea.

16. The method of claim 13, wherein the sleep apnea is obstructive sleep apnea.

17. A method of treating sleep apnea in a subject in need thereof, comprising administering to the subject an effective amount of a pharmaceutically acceptable salt of:

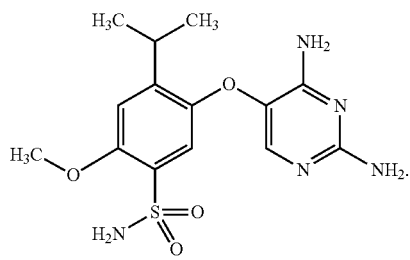 [SMILES: COc1cc(C(C)C)c(Oc2cnc(N)nc2N)cc1S(N)(=O)=O]
18. The method of claim 17, wherein the sleep apnea is central sleep apnea.
19. The method of claim 17, wherein the sleep apnea is obstructive sleep apnea.
20. The method of claim 17, wherein the sleep apnea occurs more than about 5 apneic events per hour of sleep.
\* \* \* \* \*